United States Patent
Dombrowski et al.

(10) Patent No.: US 8,747,111 B2
(45) Date of Patent: Jun. 10, 2014

(54) SUCTION HANDLE, SUCTION HANDLE ASSEMBLY, AND ORAL CARE SYSTEMS COMPRISING SAME

(75) Inventors: Alan R. Dombrowski, Woodbury, MN (US); Clark F. Bow, Dandridge, TN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/695,311

(22) PCT Filed: Apr. 27, 2011

(86) PCT No.: PCT/US2011/034127
§ 371 (c)(1),
(2), (4) Date: Oct. 30, 2012

(87) PCT Pub. No.: WO2011/137167
PCT Pub. Date: Nov. 3, 2011

(65) Prior Publication Data
US 2013/0052610 A1 Feb. 28, 2013

Related U.S. Application Data

(60) Provisional application No. 61/329,797, filed on Apr. 30, 2010.

(51) Int. Cl.
*A61C 17/06* (2006.01)
(52) U.S. Cl.
USPC .......................................................... 433/95
(58) Field of Classification Search
USPC ...................................... 433/91–96
See application file for complete search history.

(56) References Cited

U.S. PATENT DOCUMENTS

| 3,645,497 A | 2/1972 | Nyboer |
| 3,828,780 A | 8/1974 | Morrison, Jr. |
| 3,834,388 A | 9/1974 | Sauer |
| D241,476 S | 9/1976 | Lahay |
| 4,430,073 A | 2/1984 | Bemis et al. |
| 4,487,600 A | 12/1984 | Brownlie |
| 4,617,013 A | 10/1986 | Betz |
| 4,776,840 A | 10/1988 | Freitas et al. |

(Continued)

OTHER PUBLICATIONS

International Search Report PCT/US2011/034127; Jul. 15, 2011, 2 pages.

(Continued)

*Primary Examiner* — Sunil K Singh
(74) *Attorney, Agent, or Firm* — Nicole J. Einerson

(57) ABSTRACT

A suction handle, a suction handle assembly, and an oral care system. The suction handle can include a first axis oriented along a longitudinal direction, a first conduit having a first bore oriented along the first axis, and a second conduit adapted to be coupled to the first conduit, which can have a second bore oriented along the first axis. The first conduit and the second conduit can be movable with respect to one another in the longitudinal direction between a first position in which there is no fluid communication between the first and second bores, and a second position in which there is fluid communication. An actuator can be coupled to at least one of the first conduit and the second conduit that which can pivot about a second axis oriented substantially perpendicularly with respect to the first axis between a first and second actuator position.

18 Claims, 8 Drawing Sheets

(56) References Cited

U.S. PATENT DOCUMENTS

| | | | |
|---|---|---|---|
| 4,861,266 | A | 8/1989 | Ashiku |
| 4,941,872 | A | 7/1990 | Felix |
| 5,013,300 | A | 5/1991 | Williams |
| 5,019,054 | A | 5/1991 | Clement |
| 5,076,787 | A | 12/1991 | Overmyer |
| 5,267,586 | A * | 12/1993 | Jankavaara ............. 137/565.12 |
| 5,320,328 | A | 6/1994 | Decloux et al. |
| D359,118 | S | 6/1995 | Nates |
| 5,480,124 | A * | 1/1996 | Bartlett et al. ................ 251/309 |
| D378,939 | S | 4/1997 | Smith |
| 5,971,956 | A | 10/1999 | Epstein |
| 6,117,134 | A | 9/2000 | Cunningham |
| 6,129,547 | A | 10/2000 | Cise et al. |
| 6,500,142 | B1 | 12/2002 | Harreld et al. |
| 6,632,091 | B1 | 10/2003 | Cise et al. |
| 6,746,419 | B1 | 6/2004 | Arnett |
| 6,942,674 | B2 * | 9/2005 | Belef et al. .................... 606/142 |
| 7,025,755 | B2 | 4/2006 | Epstein |
| D533,274 | S | 12/2006 | Visconti |
| 7,318,814 | B2 | 1/2008 | Levine et al. |
| D571,458 | S | 6/2008 | Kataoka |
| 7,776,004 | B2 | 8/2010 | Yarger |
| D630,728 | S | 1/2011 | Dombrowski |
| D655,509 | S | 3/2012 | Dombrowski |
| 2003/0139708 | A1 | 7/2003 | Bacher |
| 2005/0175961 | A1 * | 8/2005 | March ............................. 433/91 |
| 2007/0173764 | A1 | 7/2007 | Greeson et al. |
| 2008/0145816 | A1 | 6/2008 | Hershey et al. |
| 2011/0151404 | A1 | 6/2011 | Dombrowski |
| 2011/0151405 | A1 | 6/2011 | Dombrowski |

OTHER PUBLICATIONS

Kimberly-Clark* KimVent* Oral Care q4 Kit, q2 Kit & Individual Components/Packs brochure, © 2008, 6 pgs.

Medline, Achieving Excellence in Patient Care brochure, © 2008, 23 pgs.

Sage Products Inc., Toothette Oral Care, Oral Hygiene Product Catalog, © 2010, 20 pages.

* cited by examiner

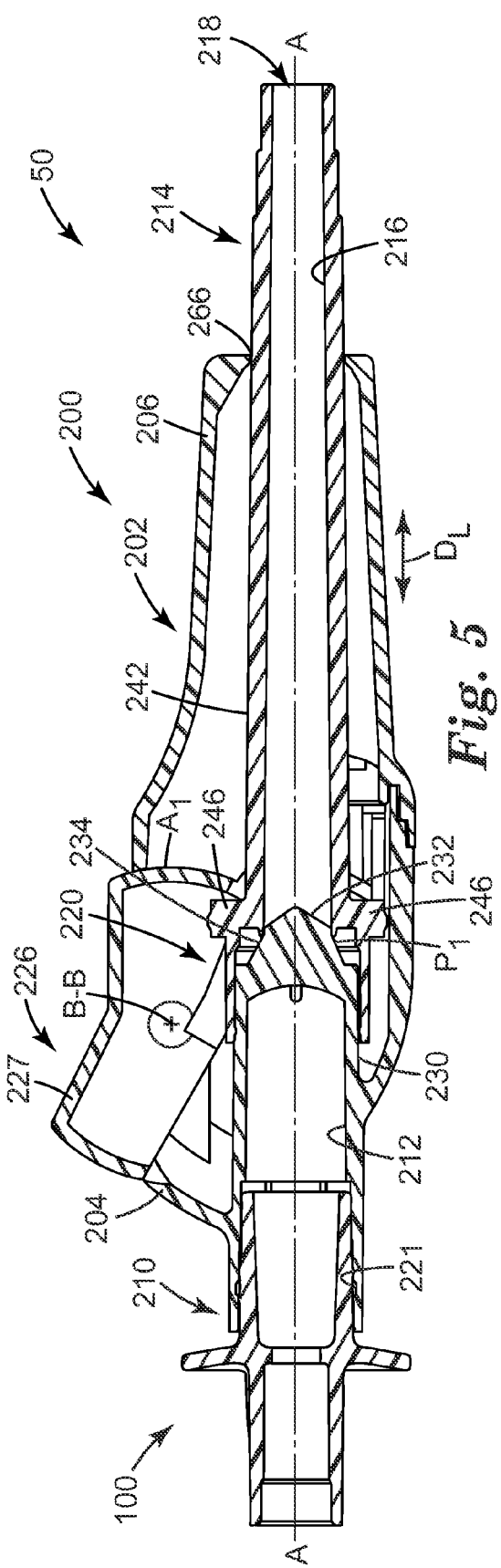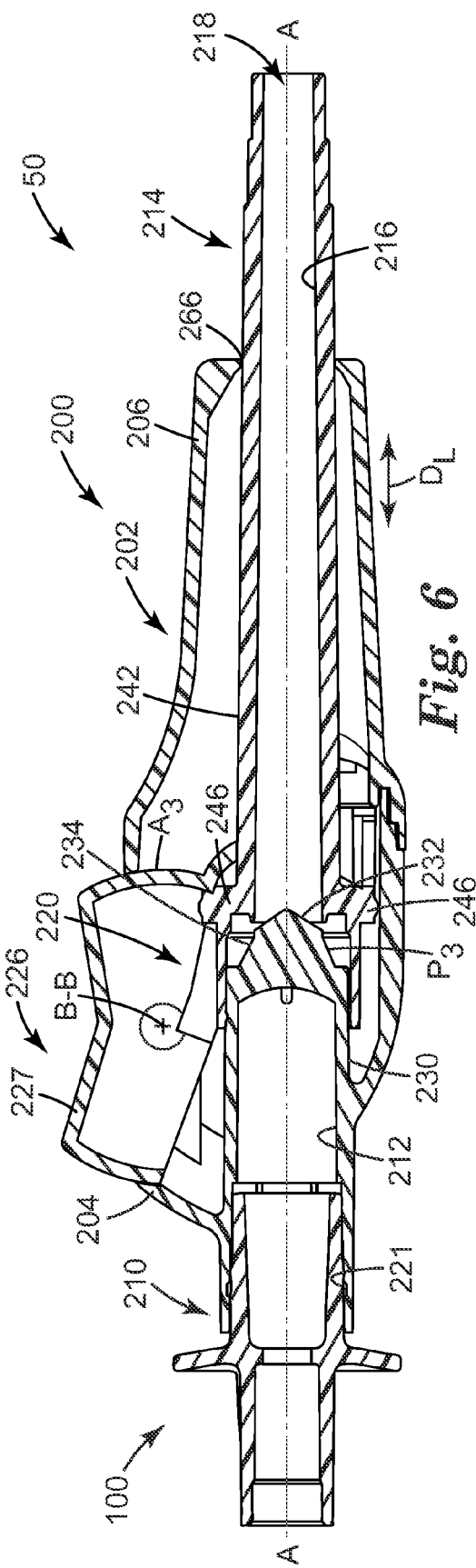

SUCTION HANDLE, SUCTION HANDLE ASSEMBLY, AND ORAL CARE SYSTEMS COMPRISING SAME

FIELD

The present disclosure generally relates to a suction handle assembly, and particularly, to a suction handle for oral care systems that can activate/deactivate and/or modulate suction for the system.

BACKGROUND

Patients who are on a ventilator for more than 48 hours can acquire an infection known as Ventilator Associated Pneumonia (VAP). As a result, it has become a standard practice to provide oral care to a ventilated patient. This can include performing various oral cleansing techniques such as brushing the teeth and oral tissues, as well as removing oral secretions via suctioning. Suctioning can occur simultaneously or sequentially with the oral cleansing techniques.

Such cleansing and/or suctioning functions can also be employed during various dental or medical procedures and/or to prepare a patient's mouth for various dental or medical procedures.

SUMMARY

In order to achieve adequate oral cleansing and suctioning of oral secretions, suction handles, such as those of the present disclosure, may need to be employed that allow a user to comfortably grasp the handle to manipulate an oral care device coupled thereto, and to easily, comfortably, and/or reliably activate, deactivate, and/or modulate suction and fluid connection with a suction source.

Some aspects of the present disclosure provide a suction handle for oral care systems. The suction handle can include a first axis oriented along a longitudinal direction, and a first conduit having a first bore oriented along the first axis. The suction handle can further include a second conduit adapted to be coupled to the first conduit. The second conduit can have a second bore oriented along the first axis. The first conduit and the second conduit can be movable with respect to one another in the longitudinal direction between a first position in which the first bore and the second bore are not in fluid communication and a second position in which the first bore and the second bore are in fluid communication. The first bore and the second bore can at least partially define a fluid path. The suction handle can further include an actuator coupled to at least one of the first conduit and the second conduit. The actuator can be pivotally movable about a second axis oriented substantially perpendicularly with respect to the first axis between a first actuator position that corresponds with the first position and a second actuator position that corresponds with the second position.

Some aspects of the present disclosure provide a suction handle for oral care systems. The suction handle can include a housing comprising an interior, a first axis oriented along a longitudinal direction, and a first conduit positioned in the interior of the housing, the first conduit having a first bore oriented along the longitudinal direction. The suction handle can further include a second conduit positioned in the interior of the housing. The second conduit can be adapted to be coupled to the first conduit, and can have a second bore oriented along the longitudinal direction. The first conduit and the second conduit can be movable with respect to one another in the longitudinal direction between a first position in which the first bore and the second bore are not in fluid communication and a second position in which the first bore and the second bore are in fluid communication. The first bore and the second bore can at least partially define a fluid path. The suction handle can further include an actuator coupled to the housing and at least one of the first conduit and the second conduit. The actuator can be pivotally movable about a second axis oriented substantially perpendicularly with respect to the first axis between a first actuator position that corresponds with the first position and a second actuator position that corresponds with the second position.

Some aspects of the present disclosure provide a suction handle for oral care systems. The suction handle can include a first axis oriented along a longitudinal direction, and a bore oriented along the first axis. The bore can at least partially define a fluid path. The suction handle can further include a valve positioned in the fluid path. The valve can be actuatable between an open position and a closed position, wherein at least a portion of the valve is movable along the first axis, such that the open position of the valve defines a first longitudinal position and the closed position of the valve defines a second longitudinal position located a longitudinal distance from the first position. The suction handle can further include an actuator positioned to actuate the valve. The actuator can be pivotally movable about a second axis oriented substantially perpendicularly with respect to the first axis between a first actuator position that corresponds with the open position of the valve and a second actuator position that corresponds with the closed position of the valve. The actuator can include an arm positioned to pivot toward or away from the first axis as the actuator pivots about the second axis.

Some aspects of the present disclosure provide an oral care system that can include a suction handle for oral care devices. The suction handle can have a proximal end adapted to be coupled to a suction source and a distal end. The suction handle can include a first axis oriented along a longitudinal direction, and a bore oriented along the first axis. The bore can at least partially define a fluid path. The suction handle can further include a valve positioned in the fluid path. The valve can be actuatable between an open position and a closed position. The suction handle can further include an actuator positioned to actuate the valve. The actuator can be pivotally movable about a second axis oriented substantially perpendicularly with respect to the first axis between a first actuator position that corresponds with the open position of the valve and a second actuator position that corresponds with the closed position of the valve. The oral care system can further include an oral care device coupled to the distal end of the suction handle.

Other features and aspects of the present disclosure will become apparent by consideration of the detailed description and accompanying drawings.

BRIEF DESCRIPTION OF THE DRAWINGS

FIG. 5 is a side cross-sectional view of the suction handle assembly of FIGS. 1-4, shown in a first position.

FIG. 6 is a side cross-sectional view of the suction handle assembly of FIGS. 1-5, shown in a third position.

DETAILED DESCRIPTION

Figure 1:
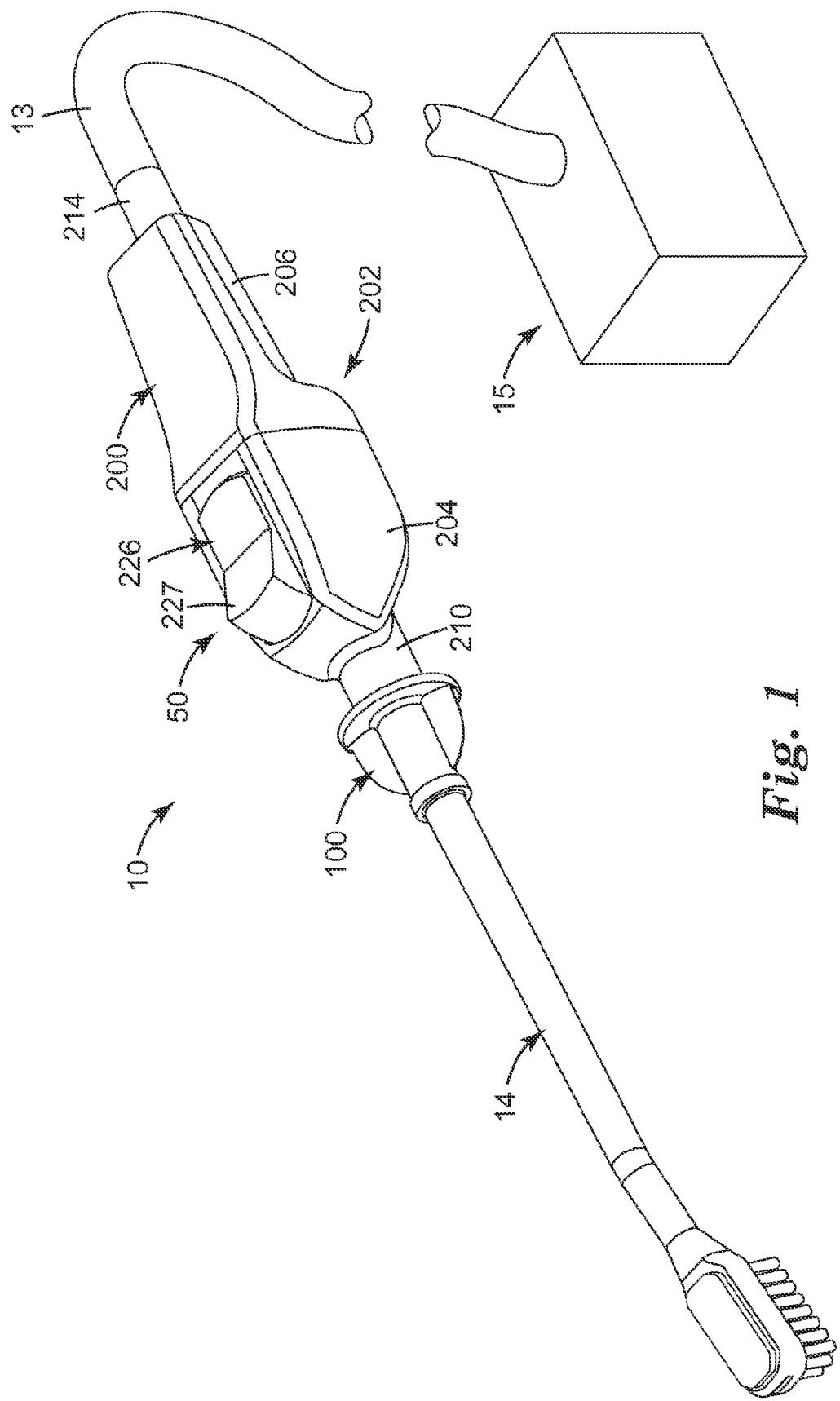
FIG. 1 is a distal perspective view of an oral care system according to one embodiment of the present disclosure, the oral care system comprising a suction handle assembly according to one embodiment of the present disclosure, the suction handle assembly comprising a suction handle and a coupling device.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the term "coupled" and variations thereof is used broadly and encompasses both direct and indirect couplings. Further, "connected" and "coupled" are not restricted to physical or mechanical connections or couplings. It is to be understood that other embodiments may be utilized, and structural or logical changes may be made without departing from the scope of the present disclosure. Furthermore, terms such as "top," "bottom," "upper," "lower," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to a suction handle and suction handle assembly for oral care systems (e.g., suction oral care systems). The suction handle can be configured to be comfortably and ergonomically grasped to manipulate an oral care device coupled thereto, for example, relative to a patient's mouth. The suction handle can be further configured to easily, comfortably, ergonomically and/or reliably activate, deactivate, and/or modulate suction and fluid connection with a suction source.

The suction handle assembly can include the suction handle and a coupling device for physically and fluidly coupling (directly or indirectly) components of an oral care system. Particularly, the coupling device can be configured to facilitate coupling and decoupling components of an oral care system. In some embodiments, the coupling device can be used to couple an oral care device and a suction, or vacuum, source. For example, in some embodiments, the coupling device can serve as an interconnect between the suction handle (i.e., that is coupled directly or indirectly to a suction source) and an oral care device of an oral care system. As a result, the coupling device of the present disclosure can include one end (e.g., a proximal end) that is configured to be coupled (directly or indirectly) to a suction source (e.g., via the suction handle of the present disclosure), and another end (e.g., a distal end) that is configured to be coupled to an oral care device that can be used to cleanse, suction, apply oral treatments, or the like, or combinations thereof. An example of a suitable coupling device is described in U.S. Patent Application No. 61/329,779, filed Apr. 30, 2010, which is incorporated herein by reference in its entirety. An example of a design of a suitable suction handle is described in U.S. Design patent application Ser. No. 29/360,786, filed Apr. 30, 2010, which is incorporated herein by reference in its entirety.

An oral care device that can be coupled to the suction handle assembly can include, but is not limited to, a variety of suction swabs, suction oral brushes (e.g., suction toothbrushes), Yankauer devices, and the like. U.S. Utility Patent Application No. 61/287,450, filed Dec. 17, 2009, and U.S. Design patent application Ser. No. 29/352,188, filed Dec. 17, 2009, describe and illustrate suitable suction swabs, each of which is incorporated herein by reference in its entirety. In addition, U.S. Utility Patent Application No. 61/288,387, filed Dec. 21, 2009, and U.S. Design patent application Ser. No. 29/352,389, filed Dec. 21, 2009, describe and illustrate suitable suction oral brushes, each of which is incorporated herein by reference in its entirety.

The terms "proximal" and "distal" are relative terms used throughout, where "proximal" refers to features, elements or points of interest that are nearer to (e.g., directed toward) a user (e.g., a medical practitioner) during use; and "distal" refers to features, elements or points of interest that are further from (e.g., directed away from) a user during use.

FIG. 1 illustrates an oral care system 10 comprising a suction handle assembly 50 that comprises a coupling device 100 and a suction handle 200. As shown in FIG. 1, the suction handle 200 can be coupled to a proximal end of the coupling device 100, and a proximal end of the suction handle 200 can be coupled, e.g., via a connector 13 and/or other fluid connection components, to a suction source 15.

The suction source 15 is only shown schematically in FIG. 1, but it should be understood that a variety of suitable suction sources or suction systems can be coupled to the oral care system 10. For example, in some embodiments, the suction source (or system) 15 can include a standard hospital or healthcare facility central suction source, with a collection canister fluidly coupled between the oral care system 10 and the central suction source. In some embodiments, various components of the suction system (e.g., canisters) can be considered to form a part of the oral care system 10.

As shown in FIG. 1, the oral care system 10 can further include an oral care device 14 that can be coupled to a distal end of the coupling device 100. In some embodiments, the oral care system 10 may not include all of the components shown in FIG. 1. For example, in some embodiments, the oral care system 10 may not include the coupling device 100, and in such embodiments, the oral care device 14 may be coupled directly to a distal end of the suction handle 200. When assembled as shown in FIG. 1, the suction handle 200 can activate/deactivate and modulate suction that is provided to the oral care device 14 from the suction source 15. The oral care device 14 is shown by way of example only; however, it should be understood that a variety of oral care devices can be employed in the oral care system 10 and coupled to the coupling device 100. The suction handle assembly 50, and particularly, the suction handle 200, is illustrated in greater detail in FIGS. 2-7. The coupling device is illustrated in greater detail in FIGS. 8-10 and described below.

Figure 2:
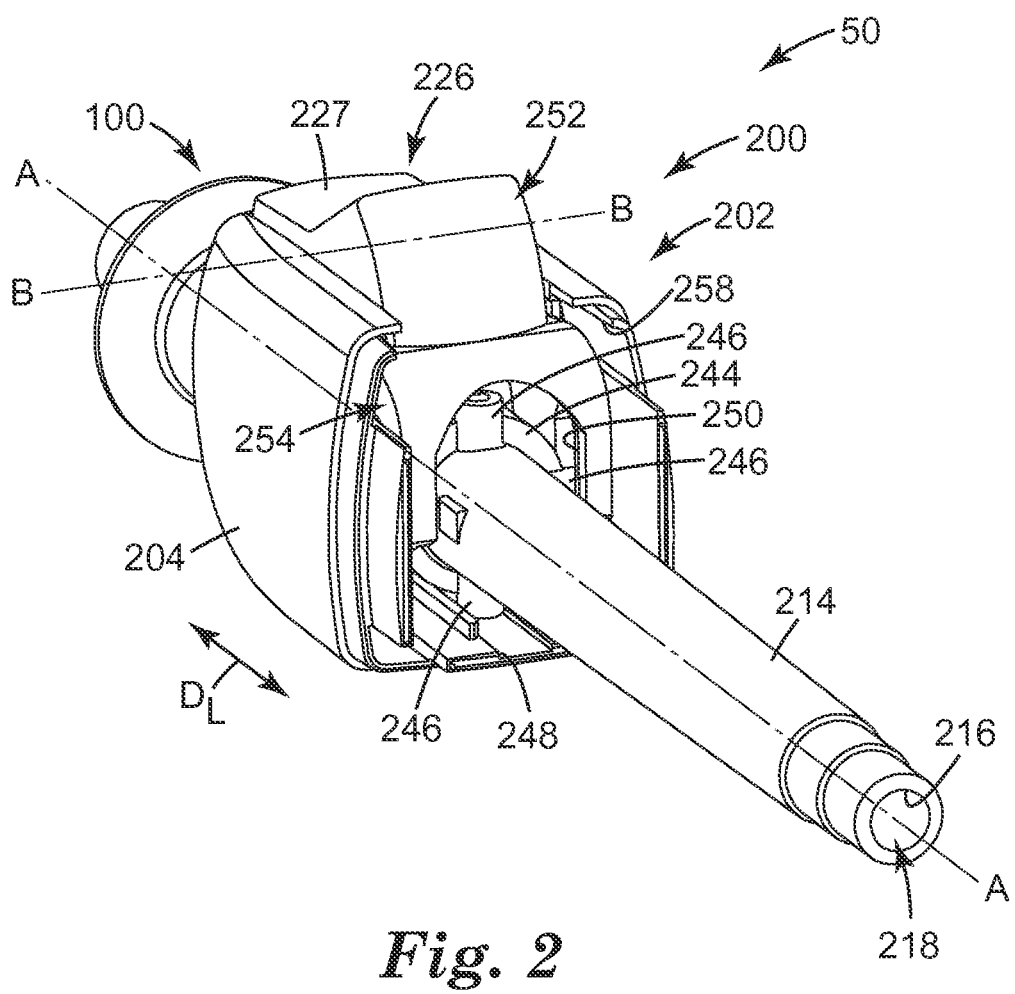
FIG. 2 is a partial proximal perspective view of the suction handle assembly of FIG. 1, with portions removed.
Figure 3:
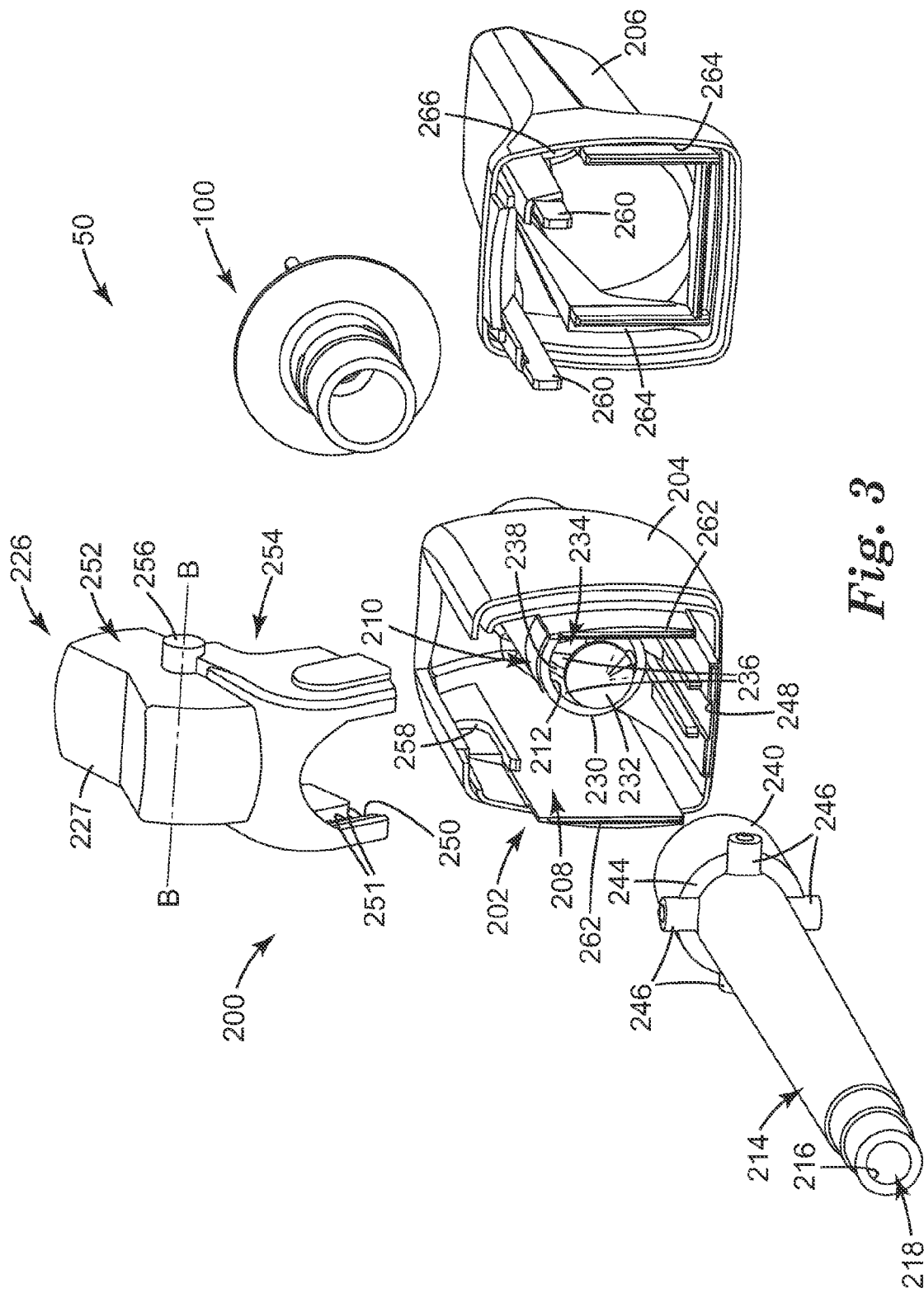
FIG. 3 is an exploded perspective view of the suction handle assembly of FIGS. 1 and 2.

With reference to FIGS. 1-7, the suction handle assembly 50 includes a first axis A-A oriented along a longitudinal direction $D_L$ (see FIGS. 2 and 4-7) of the suction handle assembly 50, such that the first axis A-A can be a central longitudinal axis through the suction handle assembly 50. As shown in FIGS. 1-7, the suction handle 200 can include a housing 202 that can define various components of the suction handle 200 or to which various components can be coupled. As best shown in FIGS. 1 and 3, in some embodiments, the housing 202 can include a first, or distal, portion 204 and a second, or proximal, portion 206 that are adapted to be coupled together to at least partially define an interior 208 (see FIG. 3) within the housing 202.

In some embodiments, the suction handle 200 (or the suction handle assembly 50) can be considered to be a single device or unitary body that includes various components or that provides various components, while in some embodiments, the components can be considered to be coupled to, integrally formed with, or located on the housing 202 of the suction handle 200. As a result, the term "coupled to" is generally used broadly throughout the present disclosure to describe how various features or elements are positioned or fashioned relative to one another, but such a description is not intended to be overly limiting. For example, it should be understood that stating that an element is coupled to the housing 202 does not mean that the housing 202 always needs to be a separate element from the element being described, but rather only indicates relative positioning between features or elements of the suction handle 200. It should be further understood that an element described as being "coupled to" the housing 202 can be provided by the housing 202, located on the housing 202, permanently attached to the housing 202, removably attached to the housing 202, or integrally formed with another portion of the suction handle 200, such as the housing 202. Furthermore, in some embodiments, the suction handle 200 may be comprised of more than one component or element, but more than one feature of the suction handle 200 can be provided by one component or element.

The suction handle 200 can further include a first conduit 210, at least a portion of which can be positioned in the interior 208 of the housing 202, and which can define a first bore 212 that is generally oriented along the first axis A-A. As shown in FIG. 1, in some embodiments, at least a portion of the first conduit 210 can extend externally with respect to the housing 202. The first conduit 210 can further be adapted to be coupled to the oral care device 14, for example, by being configured to be coupled to the coupling device 100. The distal end of the first conduit 210 can include any style of fitting necessary for coupling to the coupling device 100 and/or the oral care device 14, such as a tapered inner dimension, a bayonet-style fitting, and/or a protrusion or recess positioned to participate in a snap-fit-type engagement, which will be described in greater detail below with respect to the coupling device 100.

The suction handle 200 can further include a second conduit 214, at least a portion of which can be positioned in the interior 208 of the housing 202, which can define a second bore 216 that is generally oriented along the first axis A-A, and which can be adapted to be coupled to the first conduit 210. The second conduit 214 can be adapted to be coupled to the suction source 15, for example, by being configured to be coupled to a connector 13 or a variety of other fluid connections. As shown, a proximal end of the second conduit 214 can include a standard barbed end or fitting for coupling to standard hospital suction sources.

While the first and second conduits 210 and 214 are illustrated as being substantially tubular and circular in cross-section, such that the first and second bores 212 and 216 are substantially circular in cross-section, it should be understood that conduits 210 and 214 employing a variety of overall shapes and cross-sectional shapes can be employed, such as square, triangular, rectangular, polygonal, or a combination thereof, without departing from the spirit and scope of the present disclosure.

In some embodiments, the first conduit 210 and the second conduit 214 can be symmetrically centered about the first axis A-A. The first bore 212 and the second bore 216 can at least partially define a fluid path 218 through the suction handle 200. In some embodiments, the fluid path 218 can be substantially straight and oriented along the longitudinal direction $D_L$ and the first axis A-A of the suction handle 200.

In some embodiments, the first conduit 210 and the second conduit 214 can be referred to as a valve 220 (see FIGS. 3-7), or can define the valve 220, that can be used to control fluid flow in the fluid path 218. For example, in some embodiments, the first conduit 210 and the second conduit 214 can be movable with respect to one another in the longitudinal direction $D_L$ between a first, closed, position $P_1$ in which the first bore 212 and the second bore 216 are not in fluid communication (see FIG. 5), and a second, open, position $P_2$ in which the first bore 212 and the second bore 216 are in fluid communication (see FIG. 7). In some embodiments, as shown in FIG. 6, the first conduit 210 and the second conduit 214 can be movable to more than two positions with respect to one another, such as to a third position $P_3$ that is intermediate of the first and second positions $P_1$ and $P_2$, and in which the first bore 212 and the second bore 216 are at least partially in fluid communication with one another, i.e., a "partially open" position. The valve 220 can therefore be referred to as having at least a portion that is movable along the first axis A-A between longitudinal positions that are spaced longitudinal distances from one another along the first axis A-A.

In the illustrated embodiment, the first conduit 210 is positioned distally with respect to the second conduit 214. Furthermore, in the illustrated embodiment, the first conduit 210 is stationary with respect to the housing 202 (i.e., the first conduit 210 is coupled to (e.g., integrally formed with) the first (distal) portion 204 of the housing 202), and the second conduit 214 is movable with respect to the first conduit 210. However, it should be understood that the relative positioning, arrangement and movement of the first conduit 210 and the second conduit 214 are shown by way of example only, and other arrangements and configurations are possible in which the same or similar results are achieved, or in which the same or similar relative movement between the first conduit 210 and the second conduit 214 is achieved. In addition, in some embodiments, the fluid path 218 need not necessarily be defined by two separate and discrete conduits that each define a bore, rather, in some embodiments, the suction handle 200 can include at least one bore that is oriented along the first axis A-A (and the longitudinal direction $D_L$), and which at least partially defines the fluid path 218.

As mentioned above, in some embodiments, the first conduit 210 and the second conduit 214 can be referred to as the valve 220, or can include the valve 220. In such embodiments, the valve 220 can include, or be actuated to move between, an open position $P_1$ and a closed position $P_2$, along with any other positions that may be intermediate of the open and closed positions $P_1$ and $P_2$, such as the illustrated third position $P_3$.

As further shown in FIGS. 1-7, the suction handle 200 can further include an actuator 226 that can be coupled to at least one of the first conduit 210 and the second conduit 214, and which can be used to actuate the valve 220, or said another way, to actuate the movement between the first conduit 210 and the second conduit 214, e.g., in the longitudinal direction $D_L$ (or along the first axis A-A).

Components of the suction handle 200 or the suction handle assembly 50, such as the housing 202, the first and second conduits 210 and 214, the actuator 226, the coupling device 100, or portions thereof, can be formed of a variety of materials, such as rigid plastic materials, including but not limited to, acrylonitrile butadiene styrene (ABS), polypropylene (PP), high density polyethylene (HDPE), polystyrene (PS), polycarbonate (PC), styrene acrylonitrile (SAN), polyacetal (POM), BDS resin (a clear, impact-resistant polystyrene), polymethyl methacrylate (PMMA), polyamide (PA), polyvinyl chloride (PVC), or combinations thereof, or any of the above in combination with fillers. The components can also be formed of flexible plastic materials, including but not limited to, any of the above-described "rigid plastic materials" (e.g., HDPE) formed appropriately thin to achieve a desired level of flexibility; low density polyethylene (LDPE); linear low density polyethylene (LLDPE); very low density polyethylene (VLDPE); ethylene vinyl acetate (EVA); polyethylene methyl acrylate (EMA); blend of polypropylene and ethylene propylene diene monomer (PP-EPDM), styrene ethylene-butylene styrene (SEBS), polyurethane thermoplastic elastomer (PU), or combinations thereof. Particular utility has been found when forming the housing 202 and the first conduit 210 of ABS, the second conduit 214 of HDPE, and the actuator 226 of PP.

Figure 4:
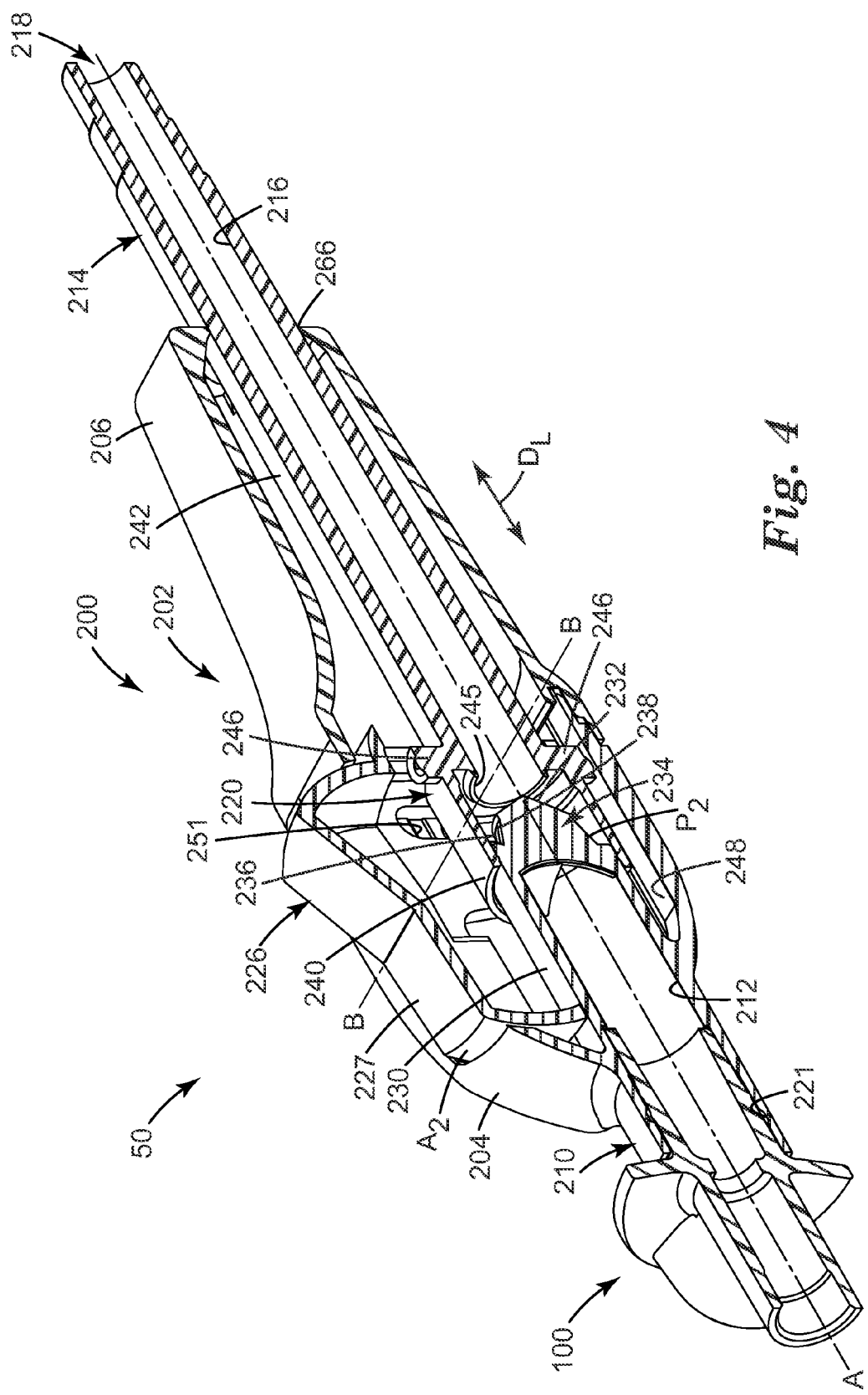
FIG. 4 is a distal perspective cross-sectional view of the suction handle assembly of FIGS. 1-3.

As shown in FIGS. 2-4, the actuator 226 can be pivotally movable about a second axis B-B that is oriented substantially perpendicularly with respect to the first axis A-A. In some embodiments, the second axis B-B can intersect the first axis A-A (e.g., such that the second axis B-B lies in the same horizontal plane as the first axis A-A). In some embodiments, the axes A-A and B-B do not necessarily intersect but are oriented perpendicularly with respect to one another (e.g., such that the second axis B-B lies in a plane parallel to the horizontal plane of the A-A axis). As shown, the actuator 226 can be positioned centrally with respect to the housing 202 (e.g., with respect to a width of the housing 202) and/or can be symmetrically centered over the first axis A-A, such that the actuator 226 lies along the same axis as the first conduit 210 and the second conduit 214. In addition, as shown, it can be preferred that the second axis B-B does not intersect the first axis A-A, but rather, that the second axis B-B is spaced a distance from the first axis A-A (e.g., above the first axis A-A), such that the actuator 226 pivots in the same plane as the first axis A-A lies. Such an arrangement can allow the actuator 226 to generally be (and operate) in line with the first axis A-A, which can improve the ergonomics and utility of the suction handle 200, and can make the suction handle 200 easier to operate.

Furthermore, in some embodiments, the actuator 226 can include one or more arms 227 that can be centered across the first axis A-A such that the arms 227 pivot toward and/or away from the first axis A-A when the actuator 226 pivots about the second axis B-B. As a result, the direction of rotation of the arms 227 can be in the same plane as the first axis A-A (and the direction of fluid flow). In the illustrated embodiment, the actuator 226 can be referred to as having one arm 227 (e.g., having two surfaces oriented at an angle with respect to one another), or as having two arms 227 oriented at an angle with respect to one another.

In some embodiments, pivoting can be defined to be no greater than 180 degrees of rotation, in some embodiments, no greater than 120 degrees, in some embodiments, no greater than 90 degrees, in some embodiments, no greater than 60 degrees, and in some embodiments, no greater than 45 degrees. That is, in some embodiments, the actuator 226, and particularly the arm 227, can pivot by no more than the angles described above.

Figure 7:
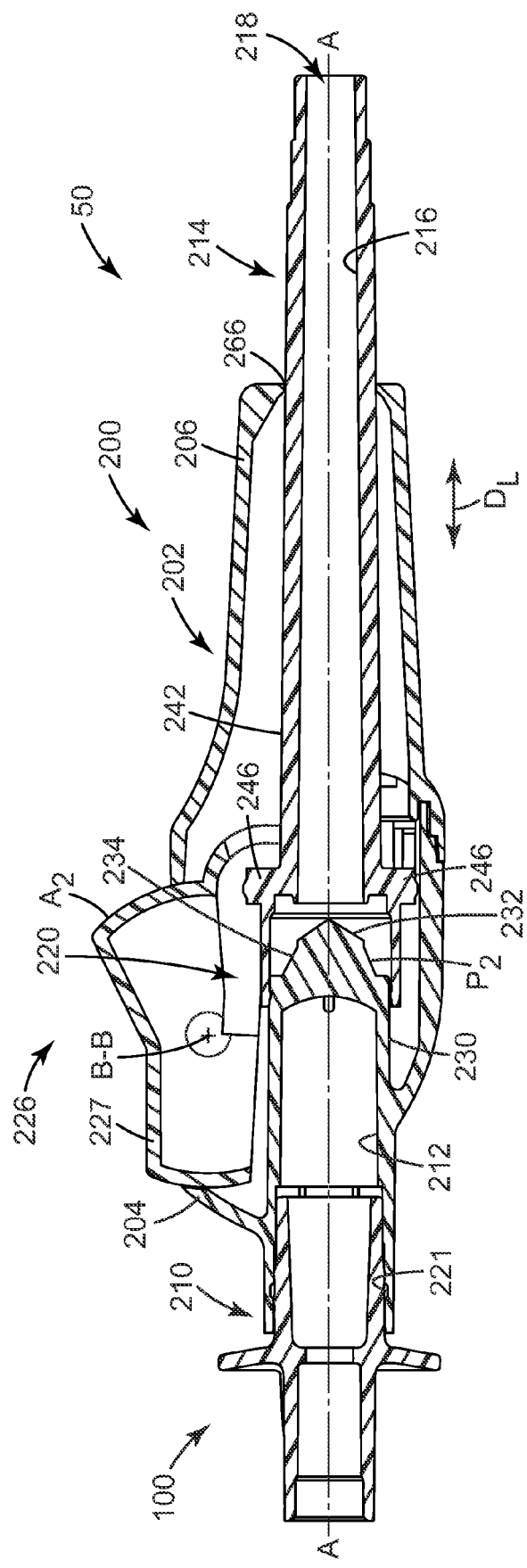
FIG. 7 is a side cross-sectional view of the suction handle assembly of FIGS. 1-6, shown in a second position.

The actuator 226 can include a variety of positions (e.g., discrete positions) that can correspond to valve positions (or relative positions between the first conduit 210 and the second conduit 214 of the illustrated embodiment). For example, as shown in FIG. 5, the actuator 226 can include a first actuator position $A_1$ that corresponds with the first position $P_1$ ("OFF"), in which the first bore 212 and the second bore 216 are not in fluid communication. As shown in FIG. 7, the actuator 226 can include a second actuator position $A_2$ that can correspond to the second position $P_2$ ("FULLY ON") in which the first bore 212 and the second bore 216 are in fluid communication. Furthermore, in some embodiments, the actuator 226 can be movable to more than two positions, such as a third actuator position $A_3$ (see FIG. 6) that can correspond to the third position $P_3$ ("PARTIALLY ON") in which the first bore 212 and the second bore 216 are at least partially in fluid communication.

As shown in FIGS. 3-7, the first conduit 210 can include a first section 230 that can be dimensioned to be received in an end of the second conduit 214. Particularly, as shown in FIGS. 4-7, the first section 230 of the first conduit 210 can be dimensioned to be received in a first section 240 of the second conduit 214 or the second bore 216. The first conduit 210 can further include a second section 232 that can take the form of (or that can include) a plug, and which can include a smaller cross-sectional dimension (e.g., diameter) or area than that of the first section 230. For example, as shown, the second section 232 can include a tapered profile. Particularly, in some embodiments, the second section 232 of the first conduit 210 can be dimensioned to be received in, or to plug, a second section 242 of the second conduit 214 (or the second bore 216). As a result, as the first conduit 210 and the second conduit 214 are moved with respect to one another in the longitudinal direction $D_L$ (e.g., along the first axis A-A) between the first position $P_1$ and the second position $P_2$, the first conduit 210 can remain coupled to the second conduit 214, and particularly, the first section 230 of the first conduit 210 can remain positioned within the first section 240 of the second conduit 214.

As shown, in some embodiments, the first conduit 210 can further include an intermediate section (which can also be referred to as a "third section") 234 located between the first section 230 and the second section 232. The intermediate section 234 can include one or more openings 236, which can allow fluid to flow between the first bore 212 and the second bore 216 when the first conduit 210 and the second conduit 214 are in fluid communication (i.e., are in the second position $P_2$ or the third position $P_3$). The openings 236 can sometimes be referred to as "transverse openings" because the openings 236 are at least somewhat formed through a sidewall of the first conduit 210. The intermediate section 234 can include one or more ribs 238 that can separate the intermediate section 234 into a desired number of openings 236. As shown, in some embodiments, the intermediate section 234 can include a tapered profile, which can cause the openings 236 to be less "transverse," such that fluid can flow more along the longitudinal direction $D_L$.

As shown in FIG. 5, when the valve 220 is closed, or the first and second conduits 210 and 214 are in the first position $P_1$, the second section 232 of the first conduit 210 can be fully seated in the second section 242 of the second conduit 214, such that the first bore 212 and the openings 236 (i.e., located in the intermediate section 234 of the first conduit 210) are not in fluid communication with the second bore 216. As shown in FIG. 6, when the valve 220 is partially opened, or the first and second conduits 210 and 214 are moved to the third position P₃, the second section 232 of the first conduit 210 is no longer fully seated in the second section 242 of the second conduit 214, and the first bore 212 and the openings 236 are at least partially in fluid communication with the second bore 216. As shown in FIG. 7, when the valve 220 is opened, or the first and second conduits 210 and 214 are moved to the second position P₂, the first bore 212 and the openings 236 are in fluid communication with the second bore 216, and the first section 230 of the first conduit 210 remains coupled to the first section 240 of the second conduit 214.

As shown in FIGS. 2 and 3, in some embodiments, the second conduit 214 can include a wall or land 244 positioned between the first section 240 and the second section 242 of the second conduit 214. Externally, the wall 244 can be oriented substantially perpendicularly with respect to the first axis A-A, as shown, or the wall 244 can be oriented at a different angle with respect to the first axis A-A. Internally, the wall 244 can include an annular inner lip or flange 245 (see FIG. 4) that can be adapted to facilitate sealing against the first conduit 210, e.g., the second section 232 of the first conduit 210. In some embodiments, the lip 245 can be formed to be thin and/or flexible (e.g., of HDPE) to facilitate sealing even when variations in dimensions are present. In some embodiments, the suction handle 200 can include an additional seal or gasket positioned between the second section 232 of the first conduit 210 and the second section 242 of the second conduit 214. For example, in some embodiments, such a gasket can be positioned adjacent the wall 244, or the wall 244 and/or the lip 245 can be configured to receive a gasket that can be press-fit into place. In such embodiments, the second conduit 214 can be described as having a receptacle, recess or pocket configured to receive a gasket. In some embodiments, such a gasket can instead be positioned on the first conduit 210. The gasket can be constructed of a thermoplastic elastomer material, nitrile rubber, an HDPE/foam, an LDPE-foam core extruded liner, another suitable gasket material, or a combination thereof. In some embodiments, the lip 245 can be sufficient for fluidly sealing (e.g., hermetically sealing) the respective portions of the first conduit 210 and the second conduit 214 without the use of a gasket. The seal, whether formed with a gasket or without the use of a gasket, can be capable of inhibiting leaks under a typical oral care system usage range of about 5-12" Hg (127-305 mm Hg).

In the illustrated embodiment, the second section 232 of the first conduit 210 and the second section 242 of the second conduit 214 include a smaller cross-sectional area (e.g., a smaller cross-sectional dimension, such a diameter) than the first section 230 of the first conduit 210 and the first section 240 of the second conduit 214, respectively.

In some embodiments, the second conduit 214 can include one or more features that facilitate coupling the second conduit 214 to the housing 202 and/or the actuator 226. As shown in FIGS. 2 and 3, in some embodiments, the second conduit 214 can include one or more outwardly-extending transverse projections 246 that can be positioned and dimensioned to be received in a bottom recess or channel 248 of the housing 202 and/or a recess or channel 250 of the actuator 226. Broadly, the projections 246 can be referred to as transverse projections 246, because they can be oriented substantially perpendicularly to the first axis A-A. In embodiments employing a circular second conduit 214, such as the illustrated embodiment, the projections 246 can be referred to as radial projections 246, and can be described as extending radially-outwardly from the second conduit 214. By way of example only, in the illustrated embodiment, the second conduit 214 includes four projections 246, equally spaced about the second conduit 214, particularly, with each projection 246 positioned 90 degrees apart about the circumference of the second conduit 214. In addition, by way of example, the projections 246 are positioned adjacent a junction between the first section 240 and the second section 242, e.g., adjacent the wall 244.

To facilitate reliable movement of the second conduit 214 relative to the first conduit 210, the projections 246 can be arranged symmetrically about the second conduit 214. As a result, in some embodiments, the second conduit 214 can include three projections 246—one to interact with the channel 248 of the housing 202, and two to interact with the channels 250 on the actuator 226. However, by including four projections 246 and spacing them equally about the second conduit 214, assembly can be simplified, because the second conduit 214 can be assembled relative to the first conduit 210 at four different rotational positions (e.g., as opposed to having only one possible option). In addition, positioning one of the projections 246 at the bottom central position of the second conduit 214 for assembly can facilitate aligning or centering the second conduit 214 with the first conduit 210, for example, along the first axis A-A.

As further shown in FIGS. 2 and 3, in some embodiments, the actuator 226 can include a first portion 252 that can be configured to be manipulated by a user to move the actuator 226 between the actuator positions, and a second portion 254 that can be configured to interact with and/or be coupled to other components of the suction handle 200, such as the housing 202 and/or the conduits 210 and 214. In the illustrated embodiment, the first portion 252 of the actuator 226 can be positioned centrally with respect to the housing 202, when assembled, to facilitate being equally operated in a left-handed configuration or a right-handed configuration. In addition, by way of example, the first portion 252 includes a rocker switch that can be depressed and pivoted in either direction (e.g., angular direction) with similar effort. In some embodiments, as shown, the rocker switch can be sized to be relatively large with respect to the housing 202 to facilitate moving between actuator positions with relative ease using a thumb or finger. The shape and dimensions of the housing 202 and the actuator 226 of the illustrated embodiment are particularly suitable for grasping the housing 202 in the palm of the hand of a user and operating the actuator 226 with a thumb. In addition, employing a rocker switch that moves between actuator positions (e.g., A₁, A₂ and A₃) by pivoting can require less operating force (e.g., via the moment arm of rotation) than other types of systems that may employ translational movement rather than rotational movement, such as systems that employ a sliding actuator.

In addition, the actuator 226 can be pivotally movable relative to the housing 202 (and the first conduit 210 and the second conduit 214) about the second axis B-B to various discrete positions. As shown in FIGS. 3 and 4, one possible way of obtaining reliability discrete actuator positions is by including one or more detent positions 251 in the channels 250. In some embodiments, the actuator 226 includes at least two detent positions 251 (e.g., which can correspond to the first and second positions P₁ and P₂). The projections 246 can each be sized and shaped to reliably remain in one of the latches or detent positions 251 in the respective channel 250 of the actuator 226, until a sufficient force is provided to overcome the force needed to move the projection 246 over an adjacent rib or protrusion, and into the next detent position 251. As such, the actuator 226 can include audible and/or tactile "clicks" or stops for confident and reliable actuator positioning.

The illustrated embodiment includes three detent positions 251 that each correspond with one of the valve positions $P_1$, $P_2$ and $P_3$, as well as the actuator positions $A_1$, $A_2$ and $A_3$. In addition, coupling the projections 246 to the actuator 226 allows the second conduit 214 to be driven by the actuator 226, such that moving the actuator 226 between its actuator positions (e.g., $A_1$, $A_2$ and $A_3$) moves the second conduit 214 relative to the first conduit 210 between the valve positions (e.g., $P_1$, $P_2$ and $P_3$). As a result, as the actuator 226 is pivoted about the second axis B-B, the movement of the second portion 254 of the actuator 226 relative to the second conduit 214, causes the projections 246 positioned in the channels 250 to move to a different detent position 251 in the channel 250, thereby causing the second conduit 214 to move longitudinally with respect to the first conduit 210. As described above and shown in the illustrated embodiment, movement of the actuator 226 can move the second conduit 214 relative to the first conduit 210 and the housing 202 between the first, second and third positions $P_1$, $P_2$ and $P_3$.

Because of the detent positions 251, the actuator 226 can be capable of latching in the discrete positions, such that when the actuator 226 has been moved to an "ON" position, an "OFF" position, or an intermediate position, for example, a user need not continue to hold the actuator 226 (e.g., the rocker switch) in the desired position. Rather, the actuator 226 will be latched in the desired position, until the user pivots the actuator 226 about the second axis B-B, as desired, to change the position of the actuator 226.

In the illustrated embodiment, the second portion 254 of the actuator 226 is configured for coupling with the housing 202 and the second conduit 214, such that when the first portion 252 is moved between the actuator positions, the second conduit 214 is moved with respect to the housing 202 and the first conduit 210. By way of example only, as shown in FIG. 3, in some embodiments the actuator 226 can include one or more outwardly-extending projections 256 that are configured to be received in corresponding channels 258 of the housing 202. By way of further example, the illustrated embodiment includes two projections 256 and two channels 258, and the projections 256 are configured to be slidably received in the channels 258, such that the projections 256 can also pivot with respect to the channels 258 to allow the actuator 226 to pivot about the second axis B-B. That is, the projections 256 can at least partially define the location of the second axis B-B about which the actuator 226 pivots.

Furthermore, to facilitate assembling the suction handle 200, and to facilitate coupling the first portion 204 of the housing 202 and the second portion 206 of the housing 202, one or both of the first portion 204 and the second portion 206 of the housing 202 can include one or more projections or recesses adapted to mate with one another. By way of example only, the second portion 206 of the housing 202 can include one or more longitudinally-extending upper projections 260 positioned near the top of the second portion 206. As shown in FIG. 3, the projections 260 can be shaped and dimensioned to be received in the channels 258 of the first portion 204 of the housing 202, for example, after the actuator projections 256 have been slid into place at distal ends of the channels 258. As can be seen in FIG. 3, in some embodiments, the projections 260 can be multi-part or include a complex or stepped shape or profile, and the channels 258 can include the mating, or negative, of such a shape or profile to facilitate coupling the projections 260 in the channels 258. In addition, by way of example only, the first portion 204 of the housing 202 of the illustrated embodiment includes two longitudinally-extending lateral projections 262 positioned adjacent sidewalls of the first portion 204 of the housing 202. The lateral projections 262 can be configured to be received in lateral recesses or channels 264 formed in the second portion 206 of the housing 202. The projections 260 and 262 and the mating recesses or channels 258 and 264 of the housing 202 allow for the first portion 204 and the second portion 206 of the housing 202 to be inter-engaged. However, such inter-engaging structures are shown by way of example, only, and it should be understood that a variety of coupling means can be employed to assemble the housing 202 of the suction handle 200.

As shown in FIGS. 4-7, the second portion 206 of the housing 202 can further include a proximal aperture 266 through which at least a portion of the second conduit 214 can extend externally of the housing 202 for coupling to the suction source 15.

The suction handle 200 can be assembled based on the above engagements or inter-engagements, namely, between the first conduit 210 and the second conduit 214; between the second conduit 214 and the housing 202; between the second conduit 214 and the actuator 226; between the actuator 226 and the housing 202; and between the first portion 204 of the housing 202 and the second portion 206 of the housing 202. As a result, the suction handle 200 can be assembled by orienting the second conduit 214 with respect to the first conduit 210 such that two projections 246 project to the sides, and two projections 246 project up and down. The bottom projection 246 in that orientation can then be lined up with the bottom channel 248 of the housing 202, and the two side projections 246 can be slid (e.g., upwardly) into the channels 250 of the actuator 226. The actuator 226 and the second conduit 214 together can then be slid along the longitudinal direction $D_L$ (e.g., and the first axis A-A), such that the first section 230 of the first conduit 210 is slid into the first section 240 of the second conduit 214, the bottom projection 246 is slid into the bottom channel 248 of the housing 202, and the projections 256 of the actuator 226 are slid into the channels 258 of the housing 202. In addition, the coupling device 100 can be coupled to the distal end of the first conduit 210 before, during, or after assembly of the suction handle 200. The resulting sub-assembly is shown in FIG. 2.

The second portion 206 of the housing 202 can then be slid over the second conduit 214 to allow at least a portion of the second conduit 214 to extend through the proximal aperture 266 formed in the second portion 206 of the housing 202. The second portion 206 of the housing 202 can then be slid toward the first portion 204 of the housing 202 for coupling therewith. Particularly, the upper projections 260 of the second portion 206 can be slid into the channels 258 of the first portion 204, and the lateral projections 262 of the first portion 204 can be slid into the lateral channels 264 of the second portion 206.

The first portion 204 and the second portion 206 can be secured together by a variety of semi-permanent or permanent coupling means, including, but not limited to, one or more of adhesives, crimps, welding (e.g., sonic (e.g., ultrasonic) welding), any thermal bonding technique (e.g., heat and/or pressure applied to one or both of the components to be coupled), snap-fit engagement, press-fit engagement, heat sealing, other suitable permanent or semi-permanent coupling means, and combinations thereof. In some embodiments, the first portion 204 and the second portion 206 of the housing 202 can be coupled via a variety of removable coupling means, including, but not limited to, one or more of screw threads, press-fit engagement (also sometimes referred to as "friction-fit engagement" or "interference-fit engagement"), snap-fit engagement, magnets, hook-and-loop fasteners, adhesives, cohesives, clamps, heat sealing, other suitable removable coupling means, and combinations thereof. One of ordinary skill in the art will recognize that some of the permanent or semi-permanent coupling means can also be adapted to be removable, and vice versa, and are categorized in this way by way of example only.

As can be appreciated by the arrangement of the components of the suction handle 200, the actuator 226 is not positioned in the fluid path 218, nor does the actuator 226 itself function to move in the fluid path 218 or to seal the fluid path 218. Rather, the actuator 226 is fluidly isolated from the fluid path 218. As a result, movement of the actuator 226 can indirectly cause fluid connection or fluid disconnection (e.g., fluid connection between the oral care device 14 and the suction source 15) in the suction handle 200 (e.g., between the first conduit 210 and the second conduit 214). In addition, at least partially because, in the illustrated embodiment, the first conduit 210 and the second conduit 214 are fluidly isolated from ambience and remain coupled together throughout movement between the first and second positions $P_1$ and $P_2$, the interior 208 of the housing 202 remains fluidly isolated from the fluid path 218 (i.e., and from the first bore 212 and the second bore 216). As a result, the interior 208 of the housing 202 and the actuator 226 can be particularly inhibited from becoming contaminated during use.

Operation of the illustrated suction handle 200 will now be described in detail with reference to FIGS. 5-7. Initially, as shown in FIG. 5, the suction handle 200 can be in an "OFF" position in which the proximal end and the distal end of the suction handle 200 are not in fluid communication with one another. In this state, the valve 220 is in the closed position, and particularly, the first conduit 210 and the second conduit 214 are in the first position $P_1$ relative to one another, such that the second section 232 of the first conduit 210 is fully seated in the second section 242 of the second conduit 214, and the first bore 212 and the second bore 216 are not in fluid communication. Furthermore, in this state, the actuator 226 is in the first actuator position $A_1$, and the transverse projections 246 of the second conduit 214 are in the top detent position 251 of the actuator 226 (not visible in FIG. 5).

As the distal portion of the rocker switch of the actuator 226 is depressed, the actuator 226 is rotated counter-clockwise about the second axis B-B, and the transverse projections 246 are moved in the channels 250 of the actuator 226 to the next detent position 251, resulting in an audible and/or tactile click or stop. This state is illustrated in FIG. 6, and as shown, the actuator 226 has been rotated to the third position $A_3$, the transverse projections 246 are now in the middle detent position 251 in the channels 250 of the actuator 226 (not visible in FIG. 6), the second conduit 214 has been moved proximally with respect to the first conduit 210 (and the housing 202) along the first axis A-A (and the longitudinal direction $D_L$), and the second section 232 of the first conduit 210 has become unseated from the second section 242 of the second conduit 214. As a result, in FIG. 6, the valve 220 is in an intermediate position, and particularly, the second conduit 214 has moved to the third position $P_3$ with respect to the first conduit 210. In this position, the first bore 212 (and the openings 236) and the second bore 216 are in fluid communication (i.e., "PARTIALLY ON").

As the distal portion of the rocker switch of the actuator 226 is depressed further, the actuator 226 is rotated counterclockwise further about the second axis B-B, and the transverse projections 246 are moved in the channels 250 of the actuator 226 to the next detent position 251, resulting in another audible and/or tactile click. This state is illustrated in FIG. 7, and as shown, the actuator 226 has been rotated to the second position $A_2$, the transverse projections 246 are now in the bottom detent position 251 in the channels 250 of the actuator 226 (see FIG. 4), the second conduit 214 has been moved further proximally with respect to the first conduit 210 (and the housing 202) along the first axis A-A (and the longitudinal direction $D_L$), and the second section 232 of the first conduit 210 has been fully removed from the second section 242 of the second conduit 214. As a result, in FIG. 7, the valve 220 is in the open position, and particularly, the second conduit 214 has moved to the second position $P_2$ with respect to the first conduit 210. In this position, the first bore 212 (and the openings 236) and the second bore 216 are in fluid communication (i.e., "FULLY ON").

The preceding steps can then be reversed by depressing the proximal portion of the actuator 226 and rotating the actuator 226 about the second axis B-B clockwise a desired amount. As the actuator 226 is moved from the second position $A_2$ back to the first position $A_1$, the audible and/or tactile clicks or stops can again be noted at each position.

One embodiment of the coupling device 100 of the present disclosure will now be described in greater detail with particular reference to FIGS. 8-10. In general, the coupling device of the present disclosure can include one end (e.g., a proximal end) that is configured to be coupled (directly or indirectly) to a suction source, and another end (e.g., a distal end) that is configured to be coupled to an oral care device that can be used to cleanse, suction, apply oral treatments, or the like, or combinations thereof.

Figure 8:
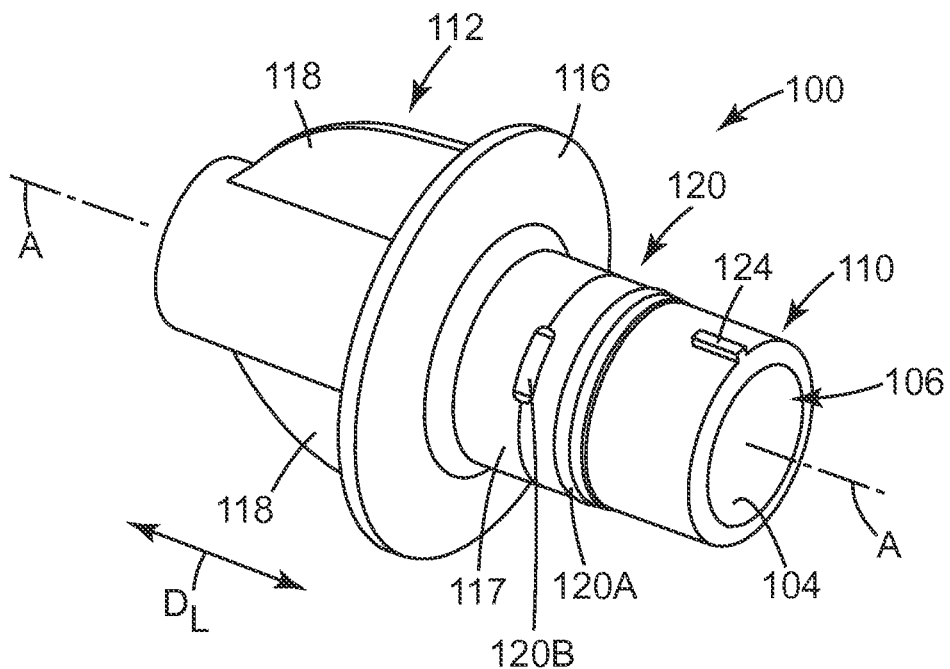
FIG. 8 is a proximal perspective view of the coupling device of FIGS. 1-7.
Figure 9:
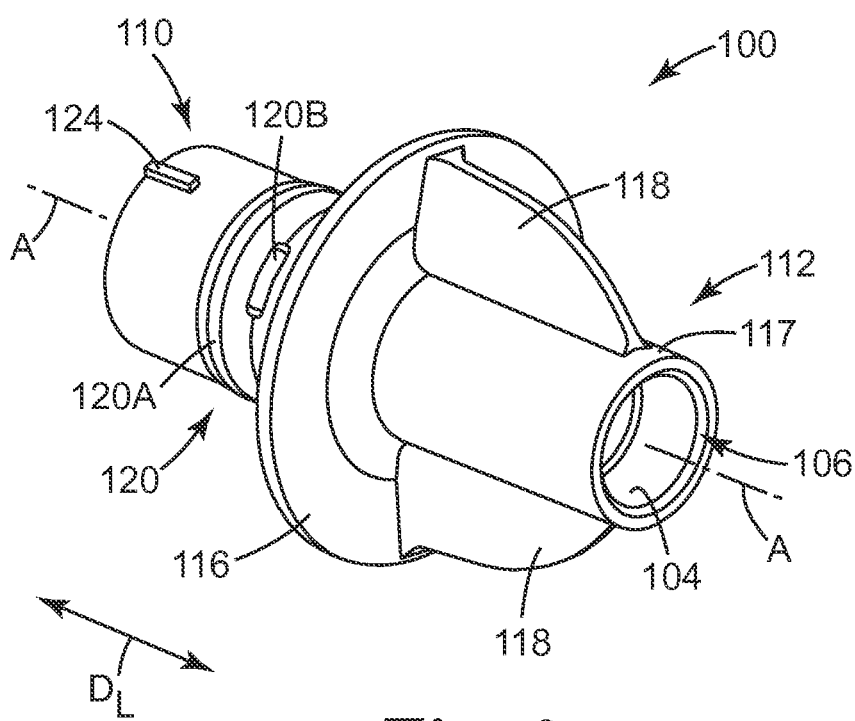
FIG. 9 is a distal perspective view of the coupling device of FIGS. 1-8.
Figure 10:
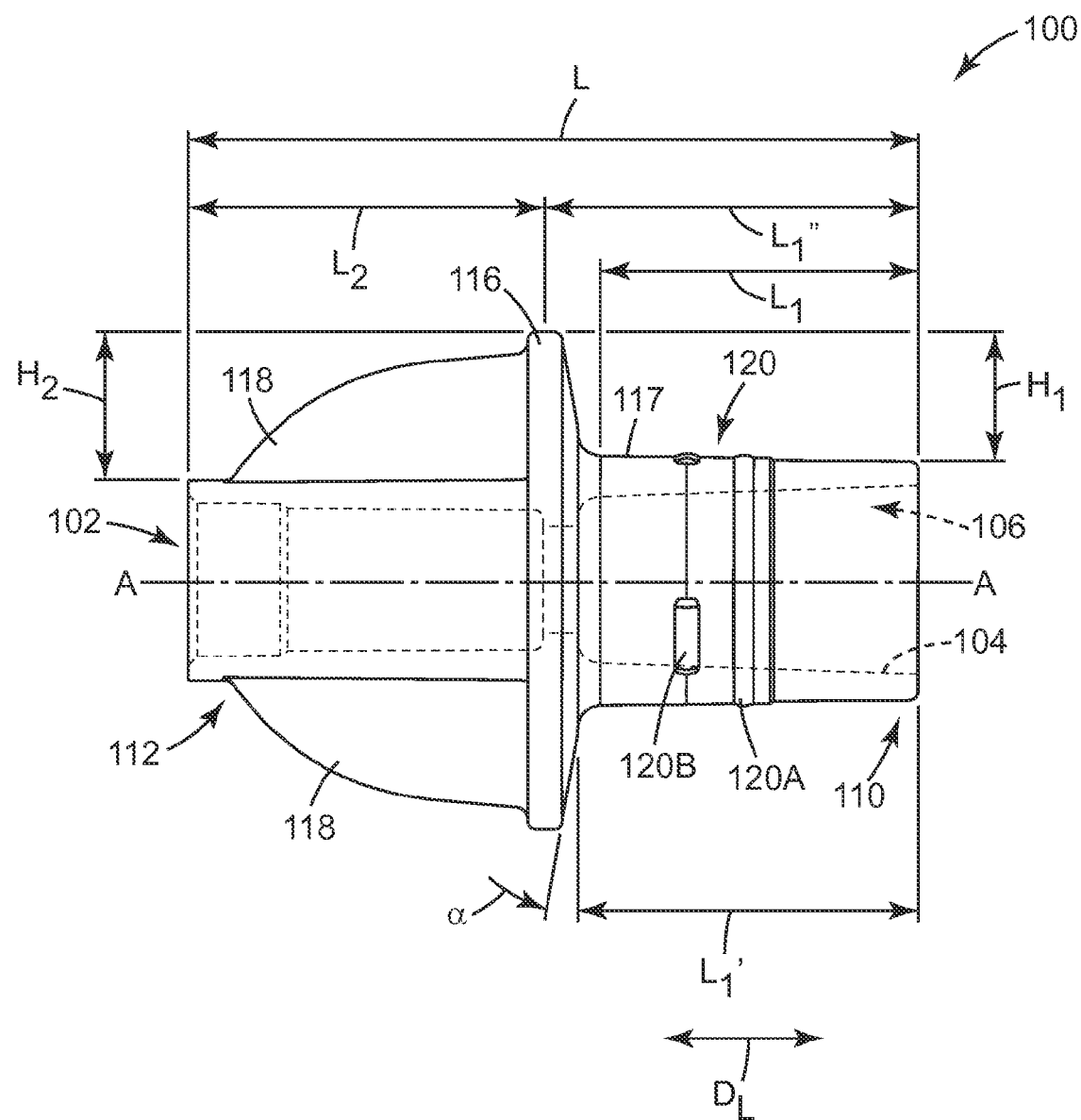
FIG. 10 is a side elevational view of the coupling device of FIGS. 1-9.

As shown in FIGS. 8-10, the coupling device 100 can include a body 102, a longitudinal direction $D_L$, and a bore 104 oriented substantially along the longitudinal direction $D_L$ and at least partially defining a fluid path 106 in the coupling device 100. The longitudinal direction $D_L$ described and illustrated with respect to the coupling device 100 can be the same longitudinal direction $D_L$ as described above with respect to the suction handle 200 or other components of the oral care system 10. As further shown, the body 102 can include a first, or proximal, portion 110 that can be adapted to be physically and fluidly coupled to the suction source 15, for example, via the suction handle 200 described above and illustrated in FIGS. 1-7 and/or other components (e.g., the connector 13) necessary for coupling to the suction source 15. The body 102 can further include a second, or distal, portion 112 that can be adapted to be physically and fluidly coupled to an oral care device, such as the oral care device 14 illustrated in FIG. 1.

Throughout the present disclosure, the first portion 110 of the coupling device 100 is described as being a proximal portion of the coupling device 100, and the second portion 112 is described as being a distal portion. However, it should be understood that in some embodiments, the first portion 110 can form a distal portion and the features shown and described as being part of the first portion 110 can be adapted for coupling to the oral care device 14, and the second portion 112 can form a proximal portion and the features shown and described as being part of the second portion 112 can be adapted for coupling to the suction handle 200.

The second portion 112 of the coupling device 100 can be configured in a variety of ways, or combination of ways, to allow the second portion 112 to be coupled to a variety of types and sizes of oral care devices 14. For example, in some embodiments, the second portion 112 can include an internal taper dimensioned to be coupled to a variety of oral care devices 14 via a press-fit-type engagement. In some embodiments, additionally or alternatively, the second portion 112 can be permanently coupled to an oral care device 14 via a variety of permanent or semi-permanent coupling means, including, but not limited to, adhesives, crimps, welding (e.g., sonic (e.g., ultrasonic) welding), any thermal bonding technique (e.g., heat and/or pressure applied to one or both of the components to be coupled), snap-fit engagement, press-fit engagement, heat sealing, other suitable permanent or semi-permanent coupling means, and combinations thereof. In some embodiments, the oral care device 14 can be removably coupled to the second portion 112 of the coupling device 100. Such removable coupling means can include, but are not limited to, screw threads, press-fit engagement (also sometimes referred to as "friction-fit engagement" or "interference-fit engagement"), snap-fit engagement, bayonet-style engagement, adhesives, cohesives, clamps, heat sealing, other suitable removable coupling means, and combinations thereof. One of ordinary skill in the art will recognize that some of the permanent or semi-permanent coupling means can also be adapted to be removable, and vice versa, and are categorized in this way by way of example only.

As a result, the coupling device 100 can be removably or permanently coupled to the oral care device 14, while also being removably coupled to the suction handle 200. For example, in some embodiments, the coupling device 100 can be permanently coupled to the oral care device 14 and removably coupled to the suction handle 200. In some embodiments, in use, the second portion 112 of the coupling device 100 can be permanently or semi-permanently coupled to the oral care device 14, while being removably coupled to the suction handle 200, such that the coupling device 100 can be disposed of along with the oral care device 14 after use.

The coupling device 100 can further include a flange 116 coupled to an outer surface 117 of the body 102 and positioned intermediately between the first portion 110 and the second portion 112. As shown in the illustrated embodiment, the flange 116 can extend outwardly from the body 102 and can be substantially continuous about the body 102. The flange 116 can be positioned to facilitate coupling and/or decoupling of the coupling device 100 from another component, such as the suction handle 200. That is, in some embodiments, the flange 116 can be configured to facilitate manual pressing on its proximal side, for example, with one or both of a thumb and forefinger (i.e., adjacent the first, or proximal, portion 110) to facilitate decoupling the first portion 110 of the coupling device 100 from the suction source 15 (e.g., by decoupling the first portion 110 from the suction handle 200).

The phrase "substantially continuous" as it relates to the flange 116 can generally refer to the flange 116 having enough continuity that allows the flange 116 to be pressed by a thumb or finger at any orientation relative to another component of the system 10, for example, a proximal component, such as the suction handle 200. That is, if the flange 116 is substantially continuous, then even if the flange 116 includes any gaps or spaces about the body 102, the gaps will be small enough not to impact being able to press the flange 116, no matter what the orientation (e.g., angular position) of the flange 116 is relative to the suction handle 200 or other component to which it is coupled.

In the illustrated embodiment, the flange 116 is substantially annular relative to the body 102. As used herein, the term "annular" or derivations thereof can refer to a structure having an outer edge and an inner edge, such that the inner edge defines an opening or defines an outer surface of other structure positioned in the opening. For example, the flange 116 can be annular, as shown, such that the body 102 is positioned within the inner edge of the flange 116. The term annular can include a variety of suitable shapes. For example, in some embodiments, an annular flange 116 can have a circular or round shape (e.g., a circular ring) or any other suitable shape, including, but not limited to, triangular, rectangular, square, trapezoidal, polygonal, etc., or combinations thereof. Furthermore, an "annulus" or annular structure of the present disclosure need not necessarily be symmetrical, but rather can be an asymmetrical or irregular shape. However, certain advantages may be possible with symmetrical and/or circular shapes. For example, in embodiments in which the flange 116 is symmetrical and uniform about the body 102 (e.g., uniform in shape and size about 360 degrees), the flange 116 can be pressed with similar ease independent of its orientation or angular position relative to other components of the oral care system 10.

In some embodiments, the coupling device 100 can be considered to be a single device or unitary body that includes various components or that provides various components (e.g., the flange 116), while in some embodiments, the components can be considered to be coupled to, integrally formed with, or located on the body 102 of the coupling device 100. As a result, the term "coupled to" is generally used broadly throughout the present disclosure to describe how various features or elements are positioned or fashioned relative to one another, but such a description is not intended to be overly limiting. For example, it should be understood that stating that an element (e.g., the flange 116) is coupled to the outer surface 117 of the body 102 does not mean that the body 102 always needs to be a separate element from the flange 116, but rather only indicates relative positioning between features or elements of the coupling device 100. It should be further understood that an element (e.g., the flange 116) described as being "coupled to" the body 102 can be provided by the body 102, located on the body 102, permanently attached to the body 102, removably attached to the body 102, or integrally formed with another portion of the coupling device 100, such as the body 102.

Furthermore, in some embodiments, the coupling device 100 may be comprised of more than one component or element, but more than one feature of the coupling device 100 can be provided by one component or element. For example, in some embodiments, the same piece or body can provide the flange 116, as well as other components, such as wings, which will be described in greater detail below. That is, in some embodiments, more than one component can be integrally formed together.

With continued reference to FIGS. 8-10, in some embodiments, the coupling device 100 can further include one or more wings 118 coupled to the outer surface 117 of the body 102, such that each of the plurality of wings 118 extends substantially along the longitudinal direction $D_L$ of the body 102. The illustrated embodiment includes a plurality of wings 118, namely, two wings 118, that are positioned opposite one another about the body 102. Specifically, in the embodiment illustrated, the body 102 is substantially tubular, and the wings 118 are diametrically opposed from one another, relative to the body 102. The wings 118 can be configured in any shape, position, or relative arrangement that allows a user to employ a twisting action to assist in coupling/decoupling the coupling device 100 to/from another component of the oral care system 10, such as the suction handle 200. For example, in addition to applying a force (e.g., pushing or pulling) in a direction along the longitudinal direction $D_L$ of the coupling device 100 to couple/decouple the coupling device 100 to/from other components, the coupling device 100 can also be turned or twisted about a longitudinal axis A-A that is oriented along or parallel to the longitudinal direction $D_L$. The longitudinal axis A-A of the coupling device 100 can be the same axis as the first axis A-A described above with respect to the suction handle 200.

The wings 118 need not be symmetrically positioned relative to other elements of the coupling device 100 or positioned exactly opposite one another relative to the body 102. Rather, the wings 118 can be configured and positioned to facilitate turning or twisting the coupling device 100 about the longitudinal axis A-A, relative to another component to which the coupling device 100 is coupled. In addition, two wings 118 are shown by way of example only; however, it should be understood that as many wings 118 as structurally possible can be employed that are suitable to facilitate twisting. While the wings 118 can be employed to twist or turn the coupling device 100 during coupling and decoupling, in some embodiments, the wings 118 can be particularly useful for decoupling.

As shown in FIGS. 8-10, in some embodiments, the wings 118 can each include a fin shape, such that the wing 118 is relatively thin (e.g., in a transverse direction or in a circumferential direction, relative to a body 102 having a circular cross-section), and its greatest dimension is in a direction along or substantially parallel to the longitudinal direction $D_L$ of the coupling device 100. Furthermore, in some embodiments, the wings 118 can include a taper along the longitudinal direction $D_L$. In the illustrated embodiment, the wings 118 each taper distally in the longitudinal direction $D_L$. Specifically, in embodiments employing a body 102 having a circular cross-section, the wings 118 can each include a radial component, relative to the body 102, that tapers along the longitudinal direction $D_L$ and a longitudinal component that extends in the longitudinal direction $D_L$. Said another way, the wings 118 can each extend substantially orthogonally with respect to the body 102 (e.g., when viewed on end) and substantially longitudinally with respect to the body 102.

As shown in FIGS. 8-10, the first portion 110 of the coupling device 100 can be dimensioned to be received within at least a portion of another component such as the suction handle 200, and the second portion 112 can be dimensioned to receive at least a portion of another component, such as that oral care device 14. It should be understood that, instead, the first portion 110 can be dimensioned to receive at least a portion of a component (such as the suction handle 200), and the second portion 112 can be dimensioned to be received in another component (such as the oral care device 14). In addition, in some embodiments, both the first portion 110 and the second portion 112 can be dimensioned to receive another component, or can both be dimensioned to be received in another component. The configuration shown in FIGS. 1-10 is shown by way of example only. In some embodiments, the illustrated configuration of the first portion 110 being dimensioned to be received and the second portion 112 being dimensioned to receive can be advantageous for achieving an effective seal, such as a fluidic or hermetic seal between components. In addition, by having at least one of the first portion 110 and the second portion 112 able to receive at least a portion of another component, a portion (i.e., the second portion 112 in the illustrated embodiment) can be exposed during use and available for grasping to assist in coupling/decoupling. For example, in the illustrated embodiment, the wings 118 can be coupled to the outer surface 117 of the body 102 and can be grasped by a user for coupling/decoupling.

Whether the first portion 110 and the second portion 112 are adapted to receive another component or be received in another component, a variety of coupling mechanisms can be employed on either end of the coupling device 100. For example, the illustrated first portion 110 that is dimensioned to be received in an end of the suction handle 200, can include at least one engagement element that is positioned to provide engagement with the suction handle 200 (or another component or the suction source 15 directly) and/or to provide a seal between the components, such as a hermetic seal, that inhibits leaking between components.

In some embodiments, the first portion 110 of the coupling device 100 can include one or more engagement elements 120 for coupling to another component of the system 10. For example, as shown in FIGS. 8-10, in some embodiments, the coupling device 100 can include a first, or proximal, engagement element 120A that is coupled to (e.g., integrally formed with) the outer surface 117 of the body 102 of the coupling device 100, and which is positioned to provide a seal between the outer surface 117 of the coupling device 100 and an inner surface of an end of the suction handle 200. For example, in some embodiments, the first engagement element 120A can include an annular protrusion that extends outwardly from the body 102 to provide a seal with an inner surface of at least a portion of the suction handle 200.

As shown in FIGS. 8-10, the first engagement element 120A can be substantially continuous about the body 102. The phrase "substantially continuous" as it relates to the engagement elements 120 can be used to described an element that extends about at least a portion of the body 102 sufficient to provide a leaktight (e.g., hermetic) fitting with another component, such as the suction handle 200. For example, in some embodiments, the first engagement element 120A is completely continuous about the body 102 to ensure a leaktight coupling, such that an additional gasket or sealing element is not needed between the coupling device 100 and the suction handle 200. In some embodiments, a "substantially continuous" engagement element can be one that provides a seal that is continuous enough to provide a fluid-tight connection. That is, at least one of the engagement elements 120 must provide an adequate seal to facilitate a functionally fluid-tight suction oral care system. In a typical hospital setting, a desired range of suction may be from 6 to 12 inches Hg (152-305 mm Hg).

As further shown in FIGS. 8-10, the first portion 110 of the coupling device 110 can further include a second, or distal, engagement element 120B that is coupled to (e.g., integrally formed with) the outer surface 117 of the body 102 of the coupling device 100, and which is configured to provide engagement with one or more cooperating features of the suction handle 200, such as engagement element 221, which is illustrated as being an undercut by way of example only (see FIGS. 4-7). For example, in some embodiments, the second engagement element 120B can include an annular protrusion that extends outwardly from the body 102 to interact or engage with a complimentary annular recess of the suction handle 200 to achieve a snap-fit-type engagement between the coupling device 100 and the suction handle 200.

As shown in FIGS. 8-10, in some embodiments, the second engagement element 120B can be discontinuous, such that the engagement element 120B does not extend fully about the body 102, but rather includes a plurality (e.g., two or more) of discrete portions or segments about the body 102. For example, in some embodiments, it is desirable for the coupling force between the coupling device 100 and the suction handle 200 (or another component of the system 10) to be great enough that the coupling device 100 and the suction handle 200 remain coupled together during use, as desired, but not so excessive that a user has great difficulty in decoupling the components. Employing a discontinuous second engagement element 120B can limit the amount of force required to decouple the coupling device 100 and the suction handle 200, while still maintaining an appropriate interference to inhibit the components from becoming undesirably decoupled during use.

In some embodiments, a straight-pull separation force or decoupling force needed to decouple the coupling device 100 from another component to which the coupling device 100 is coupled (i.e., without employing any twisting) can be no greater than about 70 N, in some embodiments, no greater than about 60 N, and in some embodiments, no greater than about 50 N. In some embodiments, a twist-and-pull separation force (e.g., employing the above-described wings 118) needed to decouple the coupling device 100 from another component can be no greater than about 50 N, in some embodiments, no greater than about 40 N, and in some embodiments, no greater than about 30 N. In some embodiments, the separation force, whether achieved with a straight-pull or a twist-pull, can range from about 20 N to about 50 N, or more particularly, from 4 lbs (18 N) to about 11 lbs (49 N).

In some embodiments employing a body 102 with a circular cross-sectional shape (as illustrated), the second engagement element 120B can be discontinuous about the body 102 in such a way that the second engagement element 120B includes portions that cover points on the body 102 that are 120 degrees apart. Maintaining coverage over points that are separated by 120 degrees can have the advantage of providing a substantially symmetrical and balanced interference between the coupling device 100 and the component to which the coupling device 100 is coupled (e.g., the suction handle 200). Such coverage can also provide the necessary coupling force to inhibit undesirable decoupling during use.

The illustrated embodiment includes two engagement elements 120 that are positioned adjacent one another and separated by a longitudinal distance—one adapted for fluid sealing, and one adapted for mechanical engagement. However, it should be understood that as few as one engagement element 120 and as many as structurally possible or necessary can instead be employed. One potential advantage of employing two engagement elements 120 that are separated by a longitudinal distance is that such an arrangement can minimize the amount of rocking or pivoting between the coupling device 100 and a component to which the coupling device 100 is coupled.

The first engagement element 120A is described as being proximal and as providing a seal, while the second engagement element 120B is described as being distal and providing engagement. However, this arrangement of elements is shown by way of example only, and it should be understood that the first engagement element 120A can instead be the element that provides engagement (e.g., snap-fit), and the second engagement element 120B can be the element that provides a seal.

By way of example only, the engagement elements 120 are illustrated as being annular protrusions that extend outwardly from the body 102, and which are integrally formed with the body 102. However, it should be understood that in embodiments in which the first portion 110 is dimensioned to receive other components (i.e., rather than be received by other components), the engagement elements 120 can instead be configured to protrude from an inner surface of the body 102 that will be coupled to an outer surface of another component. In addition, in some embodiments, the one or more engagement elements 120 may be recesses or undercuts, and the mating one or more engagement element(s) 121 on the suction handle 200 may be cooperating protrusions.

In addition, the engagement elements 120 need not be protrusions, but rather can be recesses, or a combination of protrusion or recesses, that mate with opposing and complementary features on a component of the oral care system 10 to which the coupling device 100 is to be coupled. An example of a combination of protrusions and recesses may include an engagement element 120 in which one portion about the body 102 protrudes from the body, another portion includes a recess formed in the body 102, and so on. For example, in some embodiments, the engagement element 120 can include alternating protruding and recessed sections.

The engagement elements 120 are shown by way of example only as a means for coupling the first portion 110 of the coupling device 100 to the suction source 15. However, it should be understood that other coupling means can instead be employed, including, but not limited to, providing a taper to the first portion 110 (e.g., either externally or internally), such that the first portion 110 can be press-fit onto (or into) another component, such as the suction handle 200. In addition, in some embodiments, the material forming the first portion 110 of the coupling device 100 can be softer and more pliable or deformable than the material of the portion of the component (e.g., the suction handle 200) to which the first portion 110 is being coupled. Such relative material stiffness can enhance the coupling force between the first portion 110 and the component to which the first portion 110 is coupled. While other coupling means can be employed, it should be understood that particular benefits are recognized when the first portion 110 of the coupling device 100 can be coupled to or decoupled from another component with no more than about a quarter turn or twist. For example, in some embodiments, a threaded engagement that requires a full turn or more may not be desirable.

When the coupling device 100 is coupled to (e.g., seated into) the suction handle 200, the first engagement element 120A (which can also be referred to as the "sealing engagement element") can have an interference fit with an interior seal region of the suction handle 200. In some embodiments, the first engagement element 120A can have a target dimension outer diameter (O.D.) ranging from about 0.110 cm to about 0.115 cm, particularly from about 0.113 cm to about 0.115 cm, and more particularly, about 0.115 cm. In some embodiments, the seal region of the suction handle 200 can have a target dimension inner diameter (I.D.) ranging from about 1.100 cm to about 1.105 cm, particularly, from about 1.100 cm to about 1.104 cm, and more particularly, about 1.100 cm.

The second engagement element 120B (which can also be referred to as the "snap-fit engagement element") of the coupling device 100 can reside in the mating engagement element 121 (which, in some embodiments, can be referred to as an "undercut") of the suction handle 200 when the coupling device 100 and the suction handle 200 are coupled together.

Furthermore, the most proximal end of the first portion 110 of the coupling device 100 can reside in a corresponding region of the suction handle 200 (e.g., at a depth of 0.886 cm) into the suction handle 200. In some embodiments, the second engagement element 120B can have a the target dimension O.D. ranging from about 0.125 cm to about 0.130 cm, particularly, from about 1.128 cm to about 1.130 cm, and more particularly, about 1.130 cm. The most proximal end of the first portion 110 of the coupling device 100 can have a target dimension O.D. ranging from about 1.058 cm to about 0.162 cm, particularly, from about 1.059 cm to about 1.062 cm, and particularly, about 1.062 cm. The target dimension I.D. of the internal portion of the suction handle 200 at a depth of 0.886 cm can range from about 1.065 cm to about 1.069 cm, particularly, from about 1.067 cm to about 1.068 cm, and more particularly, about 1.067 cm.

When the coupling device 100 is removed from the suction handle 200, the amount of removal force can be related to the amount of interference between the sealing engagement element 120A of the coupling device 100 and the mating seal region in the suction handle 200; as well as the interference between the snap-fit engagement element 120B of the coupling device 100 and the I.D. at the distal edge of the suction handle 200. The distal edge of the suction handle 200 can have a target dimension I.D. ranging from about 0.115 cm to about 1.118 cm, particularly, about 1.116 cm to about 1.118 cm, and more particularly, about 1.118 cm.

With continued reference to FIGS. 8-10, in some embodiments, the coupling device 100 can further include one or more ribs or protrusions 124 positioned to protrude outwardly from the outer surface 117 of the body 102. As shown, such ribs 124 can be oriented substantially in the longitudinal direction $D_L$, for example, to inhibit twisting of the coupling device 100 relative to other components (e.g., the suction handle 200) during operation. In some embodiments, the rib 124 can be referred to as a "longitudinal rib." Other components of the oral care system 10 (e.g., the suction handle 200) can have a mating or cooperating interference, rib or structure to engage or interfere with the rib 124. In some embodiments, an internal surface of the second portion 112 can include a similar rib 124 configured to inhibit undesirable turning or twisting of the coupling device 100 relative to other components (e.g., the oral care device 14) during operation.

FIG. 10 illustrates various dimensions of the coupling device 100 of the present disclosure. First, the coupling device 100 can include an overall length L (i.e., in the longitudinal direction $D_L$), that, in some embodiments, can be at least about 1.5 cm, in some embodiments, at least about 2 cm, and in some embodiments, at least about 3 cm. In some embodiments, the overall length can be about 3.2 cm.

The coupling device 100 can further include a first length $L_1$, $L_1'$ or $L_1''$ (i.e., measured from one end of the first portion 110 to a longitudinal position on the body 102 where the flange 116 begins ($L_1$); from one end of the first portion 110 to a longitudinal position where an angle of the flange 116 begins ($L_1'$); or from one end of the first portion 110 to an approximate longitudinal center of the flange 116 ($L_1''$). In some embodiments, the first length $L_1$, $L_1'$, $L_1''$ can be at least about 0.8 cm, in some embodiments, at least about 1 cm, and in some embodiments, at least about 1.2 cm. In some embodiments, the first length $L_1$, $L_1'$, $L_1''$ can be no greater than about 2 cm, in some embodiments, no greater than about 1.5 cm, and in some embodiments, no greater than about 1.3 cm. Such dimensions can provide an appropriate coupling overlap between the first portion 110 of the coupling device 100 and the suction handle 200 (or other component to which the first portion 110 is coupled).

The coupling device 100 can further include a second length $L_2$ (i.e., measured from one end of the second portion 112 to an approximate longitudinal center of the flange 116) that, in some embodiments, can be at least about 0.8 cm, in some embodiments, at least about 1 cm, and in some embodiments, at least about 1.2 cm. In some embodiments, the second length $L_2$ can be no greater than about 2 cm, in some embodiments, no greater than about 1.5 cm, and in some embodiments, no greater than about 1.3 cm. Such dimensions can provide appropriate coupling overlap between the second portion 112 of the coupling device 100 and the oral care device 114 (or other component).

Furthermore, as shown in FIG. 10, the flange 116 can include various heights measuring the distance from an outermost edge of the flange 116 to an adjacent portion of the body 102 of the coupling device 100. For example, as shown in FIG. 10, the flange 116 can include a first height $H_1$ adjacent the first portion 110 that represents the distance (e.g., a radial distance) between the first portion 110 and the outermost edge of the flange 116 on its proximal side. Said another way, the first height $H_1$ can be the maximum distance that the flange 116 extends from the body 102 on its proximal side. The flange 116 can further include a second height $H_2$ adjacent the second portion 112 that represents the distance (e.g., radial distance) between the second portion 112 and the outermost edge of the flange 116 on its distal side. Said another way, the second height $H_2$ can be the maximum distance that the flange 116 extends from the body 102 on its distal side. In some embodiments, the heights $H_1$ and $H_2$ can vary about the body 102 (e.g., if the flange 116 is not uniform about the body 102), and in some embodiments, the heights $H_1$ and $H_2$ can be uniform about the body 102 (e.g., if the flange 116 is uniform about the body 102).

Nominally, $H_1$ can be tall enough to facilitate a user's thumb and/or forefinger pushing against the flange 116 during the decoupling process. In some embodiments, one or both of the heights $H_1$ and $H_2$ can be at least about 0.5 cm, in some embodiments, at least about 1.0 cm, and in some embodiments, at least about 1.5 cm. In some embodiments, one or both of the heights $H_1$ and $H_2$ can be no greater than about 2 cm, and in some embodiments, no greater than about 1.5 cm.

As shown in FIG. 10, in some embodiments, at least a portion of the flange 116 (e.g., the distal side in the illustrated embodiment) can extend outwardly, relative to the body 102, substantially perpendicularly with respect to the longitudinal direction $D_L$ of the coupling device 100. In addition, in some embodiments, at least a portion of the flange 116 (e.g., the proximal side in the illustrated embodiment) can be canted, or oriented at a non-vertical or non-perpendicular angle, which can facilitate pressing the respective portion of the flange 116 (e.g., can facilitate pressing the proximal side to decouple the coupling device 100 from the suction handle 200).

In some embodiments, this angle can be measured relative to the first portion 110, relative to the second portion 112, or relative to a vertical (e.g., a line running perpendicular to the longitudinal axis A-A of the coupling device 100). FIG. 10 illustrates an angle $\alpha$ relative to a vertical. As a result, in some embodiments, the angle measured relative to the first portion 110 can be at least about 95 degrees, in some embodiments, at least about 100 degrees, and in some embodiments, at least about 110 degrees. In some embodiments, the angle measured relative to the second portion 112 can be no greater than about 85 degrees, in some embodiments, no greater than about 80 degrees, and in some embodiments, no greater than about 70 degrees. In some embodiments, the angle measured relative to a vertical can be at least about 5 degrees, in some embodiments, at least about 10 degrees, and in some embodiments, at least about 20 degrees. In some embodiments, the angle $\alpha$ relative to a vertical can be 11 degrees.

In some embodiments, the coupling device 100 need not be described as including a "body" 102. Rather, the coupling device 100 can be described as comprising the first portion 110, the second portion 112, the flange 116, and the wings 118. The first portion 110 and the second portion 112 can be described as together at least partially defining a longitudinal direction and a fluid path. The flange 116 can be described as being positioned intermediately of the first portion 110 and the second portion 112 and being outwardly-extending and substantially continuous. The wings 118 can be described as extending along the longitudinal direction. As a result, various components of the coupling device 100 can be described relative to one another without necessarily requiring a "body" 102. In addition, the first portion 110, the second portion 112, the flange 116, and the wings 118, or portions thereof, can be described as together at least partially defining a unitary body. For example, in some embodiments, the flange 116 and one or more of the wings 118 can be coupled together (e.g., integrally formed with one another) or provided by the same part.

The following working example is intended to be illustrative of the present disclosure and not limiting.

EXAMPLES

Example 1

Measurement of Decoupling Force

A coupling device of the present invention was manufactured by injection molding polypropylene resin (Total 3620WZ, White PC2100C, available from Total Petrochemicals of Houston, Tex.) to the design shown in FIGS. 1-4. Additionally, suction handles were manufactured for the purpose of testing the pull-off forces of the coupling device from the suction handle. The specification tolerances were 3 mil (76 micrometers) for key elements/features of outer diameters (O.D.) and internal diameters (I.D.) of both the coupling device and test suction handles. Table 1 shows the target dimensions of these element/features.

TABLE 1

Target Dimensions (cm) for Features of the Suction Handle and the Coupling Device

| Element/Feature Name | Element number in Figures | Target Dimension (cm) |
|---|---|---|
| Coupling Device - O.D. Snap-fit Engagement element | 120B | 1.130 |
| Coupling Device - O.D. Sealing Engagement element | 120A | 1.115 |
| Coupling Device - O.D. at most proximal end of first portion | 110 | 1.062 |
| Suction Handle - I.D. at distal edge | N/A | 1.118 |
| Suction Handle - I.D. Seal Region | N/A | 1.100 |
| Suction Handle - I.D. at depth of 0.886 cm | N/A | 1.067 |

The coupling device removal, or decoupling, force testing was performed to determine the amount of force necessary to remove the coupling device from a suction handle of an oral care system. In the systems tested, the coupling devices were made according to the embodiment illustrated in FIGS. 1-4, except that the coupling device did not include a longitudinal rib. The force tested was the force required to separate the suction handle from the first portion of the coupling device. Table 2 lists the actual dimensions of the suction handles and coupling devices that were tested for decoupling force. Twenty suction handles and sixty coupling devices were tested, so that each suction handle was tested with three coupling devices, for a total of 60 tests. Accordingly, as shown in Table 2, each Suction Handle-Coupling Device combination was designated by a suction handle number and a coupling device number.

TABLE 2

Actual Dimensions (cm) of the Suction Handles and Coupling Devices Tested

| Suction Handle - Coupling Device No. | Coupling Device - O.D. (cm) Snap-fit Engagement Element | Coupling Device - O.D. (cm) Sealing Engagement Element | Coupling Device - O.D. (cm) at most proximal end of first portion | Suction Handle - I.D. (cm) at distal edge | Suction Handle - I.D. (cm) at Seal Region | Suction Handle - I.D. (cm) at depth of 0.886 cm |
|---|---|---|---|---|---|---|
| Target | 1.130 | 1.115 | 1.062 | 1.118 | 1.100 | 1.067 |
| 1-1 | 1.125 | 1.113 | 1.059 | 1.115 | 1.105 | 1.067 |
| 1-2 | 1.128 | 1.114 | 1.058 | 1.115 | 1.105 | 1.067 |
| 1-3 | 1.128 | 1.113 | 1.058 | 1.115 | 1.105 | 1.067 |
| 2-4 | 1.125 | 1.113 | 1.059 | 1.116 | 1.105 | 1.068 |
| 2-5 | 1.128 | 1.113 | 1.058 | 1.116 | 1.105 | 1.068 |
| 2-6 | 1.128 | 1.114 | 1.058 | 1.116 | 1.105 | 1.068 |
| 3-7 | 1.125 | 1.113 | 1.058 | 1.116 | 1.104 | 1.067 |
| 3-8 | 1.128 | 1.113 | 1.058 | 1.116 | 1.104 | 1.067 |
| 3-9 | 1.128 | 1.113 | 1.059 | 1.116 | 1.104 | 1.067 |
| 4-10 | 1.128 | 1.113 | 1.058 | 1.115 | 1.104 | 1.067 |
| 4-11 | 1.128 | 1.113 | 1.058 | 1.115 | 1.104 | 1.067 |
| 4-12 | 1.128 | 1.113 | 1.058 | 1.115 | 1.104 | 1.067 |
| 5-13 | 1.128 | 1.113 | 1.058 | 1.115 | 1.105 | 1.067 |
| 5-14 | 1.128 | 1.113 | 1.059 | 1.115 | 1.105 | 1.067 |
| 5-15 | 1.128 | 1.114 | 1.059 | 1.115 | 1.105 | 1.067 |
| 6-16 | 1.128 | 1.114 | 1.058 | 1.116 | 1.105 | 1.067 |
| 6-17 | 1.128 | 1.113 | 1.058 | 1.116 | 1.105 | 1.067 |
| 6-18 | 1.128 | 1.113 | 1.058 | 1.116 | 1.105 | 1.067 |
| 7-19 | 1.128 | 1.113 | 1.059 | 1.115 | 1.105 | 1.067 |
| 7-20 | 1.128 | 1.114 | 1.058 | 1.115 | 1.105 | 1.067 |
| 7-21 | 1.128 | 1.113 | 1.059 | 1.115 | 1.105 | 1.067 |
| 8-22 | 1.128 | 1.114 | 1.058 | 1.115 | 1.104 | 1.067 |
| 8-23 | 1.128 | 1.113 | 1.058 | 1.115 | 1.104 | 1.067 |
| 8-24 | 1.128 | 1.113 | 1.058 | 1.115 | 1.104 | 1.067 |
| 9-25 | 1.128 | 1.113 | 1.058 | 1.115 | 1.105 | 1.068 |
| 9-26 | 1.128 | 1.113 | 1.058 | 1.115 | 1.105 | 1.068 |
| 9-27 | 1.128 | 1.114 | 1.058 | 1.115 | 1.105 | 1.068 |
| 10-28 | 1.128 | 1.113 | 1.059 | 1.116 | 1.105 | 1.067 |
| 10-29 | 1.128 | 1.113 | 1.058 | 1.116 | 1.105 | 1.067 |

TABLE 2-continued

Actual Dimensions (cm) of the Suction Handles and Coupling Devices Tested

| Suction Handle - Coupling Device No. | Coupling Device - O.D. (cm) Snap-fit Engagement Element | Coupling Device - O.D. (cm) Sealing Engagement Element | Coupling Device - O.D. (cm) at most proximal end of first portion | Suction Handle - I.D. (cm) at distal edge | Suction Handle - I.D. (cm) Seal Region | Suction Handle - I.D. (cm) at depth of 0.886 cm |
|---|---|---|---|---|---|---|
| 10-30 | 1.128 | 1.113 | 1.058 | 1.116 | 1.105 | 1.067 |
| 11-31 | 1.128 | 1.113 | 1.059 | 1.115 | 1.105 | 1.067 |
| 11-32 | 1.128 | 1.113 | 1.058 | 1.115 | 1.105 | 1.067 |
| 11-33 | 1.128 | 1.114 | 1.058 | 1.115 | 1.105 | 1.067 |
| 12-34 | 1.128 | 1.114 | 1.058 | 1.116 | 1.105 | 1.067 |
| 12-35 | 1.128 | 1.113 | 1.058 | 1.116 | 1.105 | 1.067 |
| 12-36 | 1.128 | 1.113 | 1.058 | 1.116 | 1.105 | 1.067 |
| 13-37 | 1.128 | 1.113 | 1.058 | 1.115 | 1.105 | 1.067 |
| 13-38 | 1.128 | 1.114 | 1.058 | 1.115 | 1.105 | 1.067 |
| 13-39 | 1.128 | 1.113 | 1.058 | 1.115 | 1.105 | 1.067 |
| 14-40 | 1.128 | 1.113 | 1.059 | 1.116 | 1.105 | 1.067 |
| 14-41 | 1.128 | 1.113 | 1.059 | 1.116 | 1.105 | 1.067 |
| 14-42 | 1.128 | 1.113 | 1.058 | 1.116 | 1.105 | 1.067 |
| 15-43 | 1.128 | 1.113 | 1.058 | 1.115 | 1.105 | 1.067 |
| 15-44 | 1.128 | 1.114 | 1.058 | 1.115 | 1.105 | 1.067 |
| 15-45 | 1.128 | 1.113 | 1.058 | 1.115 | 1.105 | 1.067 |
| 16-46 | 1.128 | 1.113 | 1.058 | 1.115 | 1.104 | 1.067 |
| 16-47 | 1.128 | 1.113 | 1.058 | 1.115 | 1.104 | 1.067 |
| 16-48 | 1.128 | 1.113 | 1.058 | 1.115 | 1.104 | 1.067 |
| 17-49 | 1.128 | 1.113 | 1.058 | 1.115 | 1.105 | 1.067 |
| 17-50 | 1.128 | 1.113 | 1.059 | 1.115 | 1.105 | 1.067 |
| 17-51 | 1.128 | 1.113 | 1.059 | 1.115 | 1.105 | 1.067 |
| 18-52 | 1.128 | 1.113 | 1.058 | 1.115 | 1.105 | 1.068 |
| 18-53 | 1.128 | 1.113 | 1.059 | 1.115 | 1.105 | 1.068 |
| 18-54 | 1.128 | 1.113 | 1.058 | 1.115 | 1.105 | 1.068 |
| 19-55 | 1.128 | 1.113 | 1.058 | 1.115 | 1.104 | 1.067 |
| 19-56 | 1.128 | 1.114 | 1.058 | 1.115 | 1.104 | 1.067 |
| 19-57 | 1.128 | 1.113 | 1.058 | 1.115 | 1.104 | 1.067 |
| 20-58 | 1.128 | 1.113 | 1.058 | 1.115 | 1.104 | 1.067 |
| 20-59 | 1.128 | 1.114 | 1.059 | 1.115 | 1.104 | 1.067 |
| 20-60 | 1.128 | 1.113 | 1.058 | 1.115 | 1.104 | 1.067 |

The removal or decoupling force testing was performed using a Chattillon digital force gauge, model DGFHS—100 pull tester, available from AMETEK US Gauge Division, of Largo, Fla. A coupling device holding fixture was also constructed from polypropylene to hold the coupling device during testing. The coupling device holding fixture was a cylindrical part with features designed to hold the coupling device against the flange 116 and wings 118 in a fixed position while providing a threaded female receiving opening for attachment to the pull tester. The pull tester was mounted in a vertical position on a rigid stand. Before testing, the first portion of the coupling device was coupled to the suction handle (i.e., the first portion was inserted into an end of the suction handle), and the coupling device was then inserted into the holding fixture. The holding fixture held the coupling device in position during the test and also prevented the coupling device from rotating about its longitudinal axis. The pull tester was set to report the maximum force obtained during the test, i.e. the force required to decouple the coupling device from the suction handle.

For a first force measurement, the force required to decouple the coupling device and the suction handle using only a straight pull along the longitudinal axis of the coupling device (and the suction handle) was measured. The suction handle was grasped manually and pulled downward, along the longitudinal axis of the coupling device (and the suction handle), at a rate of about 20 to about 30 in./s (about 50 to about 75 cm/s) to separate the coupling device from the suction handle.

The maximum force reading that was measured as the first force measurement is recorded in Table 3 below as "Straight Pull Retention Force."

For a second force measurement, the force required to decouple the coupling device and the suction handle using a simultaneous combination of straight pull (as described above) and a twist was measured. The "twist" applied was a ¼-inch-to-½-inch (0.6-cm-to-1.3-cm) twist or turn applied to the suction handle, relative to the coupling device and holding fixture. This can be referred to as the "Twist Pull Retention Force"—that is, the force required to separate the coupling device from the suction handle when a longitudinal pull and a twist about the longitudinal axis of the coupling device were employed, simultaneously. The force measurement was performed similarly to the first force measurement described above. It should be noted that the holding fixture does not allow the coupling device to turn while the suction handle is being twist pulled off. This accomplishes the same relative removal movement that would be applied in actual use: the suction handle in a fixed position while the coupling device is grasped by the second portion and wings, and twisted off.

The maximum force reading that was measured for the second force measurement is recorded in Table 3 below as "Twist Pull Retention Force."

As can be seen by the forces recorded in Table 3, there was a significant reduction in the force required to decouple the coupling device and the suction handle when a twist and pull were simultaneously employed (i.e., comparing "Straight Pull Retention" forces to "Twist Pull Retention" forces). The forces were recorded in pounds (lbs) and converted to Newtons (N). An average and standard deviation were calculated for each of the Straight Pull Retention force and the Twist Pull Retention force.

TABLE 3

Decoupling Pull Force Measurements (in lbs and N).

| Coupling device No. | Straight Pull Retention Force (lbs) | Twist Pull Retention Force (lbs) | Straight Pull Retention Force (N) | Twist Pull Retention Force (N) |
|---|---|---|---|---|
| 1 | 13.9 | 4.2 | 61.8 | 18.7 |
| 2 | 13.9 | 6.7 | 61.8 | 29.8 |
| 3 | 12.4 | 5.8 | 55.2 | 25.7 |
| 4 | 13.5 | 5.5 | 60.0 | 24.5 |
| 5 | 13.4 | 7.6 | 59.6 | 33.8 |
| 6 | 13.3 | 5.3 | 59.2 | 23.6 |
| 7 | 14.4 | 6.8 | 64.1 | 30.2 |
| 8 | 14.3 | 5.0 | 63.6 | 22.2 |
| 9 | 12.8 | 6.5 | 56.9 | 28.9 |
| 10 | 15.5 | 5.9 | 68.9 | 26.2 |
| 11 | 13.8 | 6.8 | 61.4 | 30.2 |
| 12 | 12.2 | 6.0 | 54.3 | 26.7 |
| 13 | 13.6 | 7.4 | 60.5 | 32.9 |
| 14 | 12.2 | 5.9 | 54.3 | 26.2 |
| 15 | 12.1 | 5.5 | 53.8 | 24.5 |
| 16 | 13.8 | 7.2 | 61.4 | 32.0 |
| 17 | 15.0 | 9.2 | 66.7 | 40.9 |
| 18 | 13.1 | 5.3 | 58.3 | 23.6 |
| 19 | 14.4 | 6.6 | 64.1 | 29.4 |
| 20 | 12.4 | 5.9 | 55.2 | 26.2 |
| 21 | 11.7 | 10.0 | 52.0 | 44.5 |
| 22 | 13.3 | 6.2 | 59.2 | 27.6 |
| 23 | 13.3 | 6.8 | 59.2 | 30.2 |
| 24 | 12.1 | 6.4 | 53.8 | 28.5 |
| 25 | 14.3 | 7.4 | 63.6 | 32.9 |
| 26 | 13.1 | 6.5 | 58.3 | 28.9 |
| 27 | 12.3 | 5.5 | 54.7 | 24.5 |
| 28 | 15.3 | 7.3 | 68.1 | 32.5 |
| 29 | 13.1 | 5.7 | 58.3 | 25.4 |
| 30 | 11.9 | 6.5 | 52.9 | 28.9 |
| 31 | 14.0 | 5.5 | 62.3 | 24.5 |
| 32 | 13.0 | 6.1 | 57.8 | 27.1 |
| 33 | 12.2 | 5.0 | 54.3 | 22.2 |
| 34 | 13.3 | 6.0 | 59.2 | 26.7 |
| 35 | 12.0 | 4.0 | 53.4 | 17.8 |
| 36 | 10.9 | 5.3 | 48.5 | 23.6 |
| 37 | 14.5 | 5.4 | 64.5 | 24.0 |
| 38 | 13.6 | 5.9 | 60.5 | 26.2 |
| 39 | 12.2 | 8.6 | 54.3 | 38.3 |
| 40 | 15.0 | 7.0 | 66.7 | 31.1 |
| 41 | 13.4 | 6.2 | 59.6 | 27.6 |
| 42 | 12.9 | 6.9 | 57.4 | 30.7 |
| 43 | 13.3 | 6.6 | 59.2 | 29.4 |
| 44 | 12.2 | 4.7 | 54.3 | 20.9 |
| 45 | 11.5 | 4.3 | 51.2 | 19.1 |
| 46 | 14.5 | 4.6 | 64.5 | 20.5 |
| 47 | 14.0 | 5.3 | 62.3 | 23.6 |
| 48 | 12.2 | 7.8 | 54.3 | 34.7 |
| 49 | 14.7 | 7.1 | 65.4 | 31.6 |
| 50 | 13.7 | 5.1 | 60.9 | 22.7 |
| 51 | 13.6 | 5.1 | 60.5 | 22.7 |
| 52 | 13.4 | 6.0 | 59.6 | 26.7 |
| 53 | 13.5 | 6.0 | 60.0 | 26.7 |
| 54 | 12.1 | 6.5 | 53.8 | 28.9 |
| 55 | 14.3 | 6.3 | 63.6 | 28.0 |
| 56 | 13.4 | 5.8 | 59.6 | 25.8 |
| 57 | 12.5 | 4.6 | 55.6 | 20.5 |
| 58 | 14.2 | 4.9 | 63.2 | 21.8 |
| 59 | 12.1 | 6.7 | 53.8 | 29.8 |
| 60 | 12.1 | 5.8 | 53.8 | 25.8 |
| Average | 13.2 | 6.1 | 58.9 | 27.3 |
| Std Dev | 1.0 | 1.1 | 4.6 | 5.1 |
| min | 10.9 | 4.0 | 48.5 | 17.8 |
| max | 15.5 | 10.0 | 68.9 | 44.5 |

EMBODIMENTS

Some embodiments of the present disclosure that are contemplated, include:

1. A suction handle for oral care systems, the suction handle comprising:
a first axis oriented along a longitudinal direction;
a first conduit having a first bore oriented along the first axis;
a second conduit adapted to be coupled to the first conduit, the second conduit having a second bore oriented along the first axis, the first conduit and the second conduit being movable with respect to one another in the longitudinal direction between a first position in which the first bore and the second bore are not in fluid communication and a second position in which the first bore and the second bore are in fluid communication, the first bore and the second bore at least partially defining a fluid path; and
an actuator coupled to at least one of the first conduit and the second conduit, the actuator being pivotally movable about a second axis oriented substantially perpendicularly with respect to the first axis between a first actuator position that corresponds with the first position and a second actuator position that corresponds with the second position.

2. A suction handle for oral care systems, the suction handle comprising:
a housing comprising an interior;
a first axis oriented along a longitudinal direction;
a first conduit positioned in the interior of the housing, the first conduit having a first bore oriented along the longitudinal direction;
a second conduit positioned in the interior of the housing, the second conduit adapted to be coupled to the first conduit, the second conduit having a second bore oriented along the longitudinal direction, the first conduit and the second conduit being movable with respect to one another in the longitudinal direction between a first position in which the first bore and the second bore are not in fluid communication and a second position in which the first bore and the second bore are in fluid communication, the first bore and the second bore at least partially defining a fluid path; and
an actuator coupled to the housing and at least one of the first conduit and the second conduit, the actuator being pivotally movable about a second axis oriented substantially perpendicularly with respect to the first axis between a first actuator position that corresponds with the first position and a second actuator position that corresponds with the second position.

3. A suction handle for oral care systems, the suction handle comprising:
a first axis oriented along a longitudinal direction;
a bore oriented along the first axis, the bore at least partially defining a fluid path;
a valve positioned in the fluid path, the valve actuatable between an open position and a closed position, wherein at least a portion of the valve is movable along the first axis, such that the open position of the valve defines a first longitudinal position and the closed position of the valve defines a second longitudinal position located a longitudinal distance from the first position; and
an actuator positioned to actuate the valve, the actuator being pivotally movable about a second axis oriented substantially perpendicularly with respect to the first axis between a first actuator position that corresponds with the open position of the valve and a second actuator position that corresponds with the closed position of the valve, the actuator including an arm positioned to pivot toward or away from the first axis as the actuator pivots about the second axis.

4. An oral care system comprising:
a suction handle for oral care devices, the suction handle having a proximal end adapted to be coupled to a suction source and a distal end, the suction handle comprising:
 a first axis oriented along a longitudinal direction,
 a bore oriented along the first axis, the bore at least partially defining a fluid path,
 a valve positioned in the fluid path, the valve actuatable between an open position and a closed position, and
 an actuator positioned to actuate the valve, the actuator being pivotally movable about a second axis oriented substantially perpendicularly with respect to the first axis between a first actuator position that corresponds with the open position of the valve and a second actuator position that corresponds with the closed position of the valve; and
an oral care device coupled to the distal end of the suction handle.

5. A suction handle for oral care devices, the suction handle comprising:
 a first axis oriented along a longitudinal direction;
 a bore oriented along the first axis, the bore at least partially defining a fluid path;
 a valve positioned in the fluid path, the valve actuatable between an open position and a closed position; and
 an actuator positioned to actuate the valve, the actuator being pivotally movable about a second axis oriented substantially perpendicularly with respect to the first axis between a first actuator position that corresponds with the open position of the valve and a second actuator position that corresponds with the closed position of the valve.

6. A suction handle for oral care devices, the suction handle comprising:
 a first axis oriented along a longitudinal direction;
 a bore oriented along the first axis, the bore at least partially defining a fluid path;
 a valve positioned in the fluid path, the valve actuatable between an open position and a closed position; and
 an actuator positioned to actuate the valve, the actuator being pivotally movable about a second axis oriented substantially perpendicularly with respect to the first axis between a first actuator position that corresponds with the open position of the valve and a second actuator position that corresponds with the closed position of the valve, wherein the second axis is spaced a distance from the first axis such that the first axis and the second axis do not intersect, and such that the actuator pivots in a plane in which the first axis also lies.

7. The suction handle of embodiment 1 or embodiment 2, wherein the first bore and the second bore are centered with respect to the first axis.

8. The suction handle of any of embodiments 1, 2 and 7, wherein the second conduit is adapted to be coupled to a suction source.

9. The suction handle of any of embodiments 1, 2, 7 and 8, wherein the second conduit is dimensioned to receive and end of the first conduit.

10. The suction handle of any of embodiments 1, 2 and 7-9, wherein the first conduit is adapted to be coupled to an oral care device.

11. The suction handle of any of embodiments 1, 2 and 7-10, wherein the first conduit and the second conduit together define a valve.

12. The suction handle of any of embodiments 1, 2 and 7-11, wherein the actuator is fluidly isolated from the first conduit and the second conduit.

13. The suction handle of any of embodiments 1, 2 and 7-12, wherein the actuator is configured to move the second conduit with respect to the first conduit between the first position and the second position.

14. The suction handle of any of embodiments 1, 2 and 7-13, wherein the first conduit includes at least one transverse opening in fluid communication with the first bore.

15. The suction handle of any of embodiments 1, 2 and 7-14, wherein the actuator includes a third actuator position between the first actuator position and the second actuator position in which the first bore is at least partially in fluid communication with the second bore.

16. The suction handle of any of embodiments 1, 2 and 7-15, wherein the second conduit includes at least one projection dimensioned to be received in a channel of the actuator.

17. The suction handle of embodiment 16, wherein the second conduit includes four projections equally spaced about a longitudinal axis of the second conduit.

18. The suction handle of embodiment 16 or embodiment 17, wherein the channel of the actuator includes a plurality of detent positions, and wherein the at least one projection of the second conduit is configured to move between the plurality of detent positions as the actuator pivots about the second axis.

19. The suction handle of any of embodiments 1, 2 and 7-18, wherein the second conduit includes a first section having a first cross-sectional area and a second section having a second cross-sectional area that is less than the first cross-sectional area.

20. The suction handle of embodiment 19, wherein the first conduit includes a first section dimensioned to be received in the first section of the second conduit and a second section dimensioned to be received in the second section of the second conduit.

21. The suction handle of embodiment 20, wherein the second section of the first conduit has a tapered profile.

22. The suction handle of embodiment 20 or embodiment 21, wherein the second section of the first conduit includes a plug.

23. The suction handle of any of embodiments 20-22, wherein the first conduit further includes an intermediate section located between the first section and the second section.

24. The suction handle of embodiment 22, wherein the first conduit includes at least one transverse opening in fluid communication with the first bore, and wherein the at least one transverse opening is located in the intermediate section of the first conduit.

25. The suction handle of embodiment 23 or embodiment 24, wherein the intermediate section has a tapered profile.

26. The suction handle of any of embodiments 20-25, wherein:
 the second section of the first conduit is fully seated in the second section of the second conduit when the first conduit and the second conduit are in the first position with respect to one another, such that the first bore is not in fluid communication with the second bore, and
 the second section of the first conduit is not fully seated in the second section of the second conduit when the first conduit and the second conduit are in the second position with respect to one another, such that the first bore is in fluid communication with the second bore.

27. The suction handle of any of embodiments 19-26, wherein the second conduit includes a wall positioned between the first section and the second section, and further comprising a gasket positioned adjacent the wall in the first section of the second conduit.

28. The suction handle of any of embodiments 1, 2 and 7-27, wherein the second conduit includes a lip positioned to seal against at least a portion of the first conduit when the first conduit and the second conduit are in the first position.

29. The suction handle of any of embodiments 2 and 7-28, wherein the interior of the housing is fluidly isolated from the first conduit and the second conduit.

30. The suction handle of any of embodiments 2 and 7-29, wherein the first conduit is coupled to the housing and the second conduit is movable with respect to the first conduit and the housing.

31. The suction handle of any of embodiments 2 and 7-30, wherein the actuator is coupled to the housing and pivots with respect to the housing.

32. The suction handle of any of embodiments 2 and 7-31, wherein the second conduit includes at least one transverse projection dimensioned to be received in a channel of the housing, and wherein the at least one transverse projection is positioned adjacent a junction between a first section and a second section of the second conduit.

33. The suction handle of any of embodiments 2 and 7-32, wherein the actuator includes at least one projection dimensioned to be slidably received in a channel of the housing.

34. The suction handle of embodiment 33, wherein the at least one projection defines at least a portion of the axis about which the actuator pivots.

35. The suction handle of any of embodiments 2 and 7-34, wherein the housing includes a first portion and a second portion, and wherein the first conduit is integrally formed with the first portion of the housing.

36. The suction handle of embodiment 35, wherein at least one of the first portion and the second portion of the housing includes at least one longitudinally-extending projection configured to be received in a recess of the other of the second portion and the first portion of the housing, respectively.

37. The suction handle of embodiment 35 or embodiment 36, wherein the first portion of the housing includes at least one longitudinally-extending projection dimensioned to be received in a recess of the second portion of the housing, and wherein the second portion of the housing includes at least one longitudinally-extending projection dimensioned to be received in a recess of the first portion of the housing.

38. The suction handle of any of embodiments 2 and 7-37, wherein the actuator is symmetrically centered with respect to a width of the housing.

39. The suction handle of any of the preceding embodiments, wherein the actuator is movable between at least two discrete positions.

40. The suction handle of any of the preceding embodiments, wherein the actuator is centered with respect to the first axis.

41. The suction handle of any of the preceding embodiments, wherein the actuator is positioned relative to the fluid path such that the actuator pivots in line with the first axis.

42. The suction handle of any of the preceding embodiments, wherein the first axis lies in a plane, and wherein the actuator pivots in the plane toward or away from the first axis.

43. The suction handle of any of the preceding embodiments, wherein the actuator is fluidly isolated from the fluid path.

44. The suction handle of any of the preceding embodiments, wherein the actuator includes a third actuator position between the first actuator position and the second actuator position.

45. The suction handle of any of the preceding embodiments, wherein the actuator pivots about the second axis by no more than about 90 degrees when moving between the first actuator position and the second actuator position.

46. A suction handle assembly comprising the suction handle of any of the preceding embodiments, and a coupling device coupled to the suction handle.

47. An oral care system comprising:
   the suction handle of any of the preceding embodiments; and
   an oral care device coupled to a distal end of the suction handle.

48. The oral care system of embodiment 47, further comprising a coupling device coupled between the suction handle and the oral device, a first portion of the coupling device adapted to be coupled to the suction handle and a second portion of the coupling device adapted to be coupled to the oral care device.

49. The suction handle assembly of embodiment 46 or the oral care system of embodiment 48, wherein physical coupling between the suction handle and the coupling device defines a fluid connection, and wherein the fluid connection is free of gaskets.

50. The suction handle assembly or oral care system of any of embodiments 46 and 48-49, wherein the coupling device comprises:
   a body having a longitudinal direction and a bore that at least partially defines a fluid path, wherein the body includes a first portion adapted to be coupled to a suction source and a second portion adapted to be coupled to an oral care device;
   a flange coupled to an outer surface of the body and positioned intermediately between the first portion and the second portion, the flange being outwardly-extending and substantially continuous about the body; and
   a plurality of wings coupled to the outer surface of the body such that each of the plurality of wings extends substantially along the longitudinal direction of the body.

51. The suction handle assembly or oral care system of embodiment 50, wherein the first portion of the body further comprises a first engagement element positioned to provide a seal, the first engagement element being substantially continuous about the body and comprising at least one of a protrusion and a recess.

52. The suction handle assembly or oral care system of embodiment 51, wherein the first engagement element includes an annular protrusion.

53. The suction handle assembly or oral care system of embodiment 51 or embodiment 52, wherein the first portion further comprises a second engagement element positioned adjacent the first engagement element comprising at least one of a protrusion and a recess.

54. The suction handle assembly or oral care system of embodiment 53, wherein the second engagement element includes an annular protrusion.

55. The suction handle assembly or oral care system of embodiment 53 or embodiment 54, wherein the second engagement element is discontinuous.

56. The suction handle assembly or oral care system of any of embodiments 53-55, wherein the second engagement element is configured to provide a snap-fit-type engagement.

57. The suction handle assembly or oral care system of any of embodiments 53-56, wherein at least one of the first engagement element and the second engagement element are integrally formed with the body.

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure. Various features and aspects of the present disclosure are set forth in the following claims.

What is claimed is:

1. A suction handle for oral care systems, the suction handle comprising:
   a housing comprising an interior;
   a first axis oriented along a longitudinal direction;
   a first conduit positioned in the interior of the housing, the first conduit having a first bore oriented along the longitudinal direction;
   a second conduit positioned in the interior of the housing, the second conduit adapted to be coupled to the first conduit, the second conduit having a second bore oriented along the longitudinal direction, the first conduit and the second conduit being movable with respect to one another in the longitudinal direction between a first position in which the first bore and the second bore are not in fluid communication and a second position in which the first bore and the second bore are in fluid communication, the first bore and the second bore at least partially defining a fluid path; and
   an actuator coupled to the housing and at least one of the first conduit and the second conduit, the actuator being pivotally movable about a second axis oriented substantially perpendicularly with respect to the first axis between a first actuator position that corresponds with the first position and a second actuator position that corresponds with the second position;
   wherein the interior of the housing is fluidly isolated from the fluid path when the first conduit and the second conduit are in the first position and the second position; and
   wherein the second conduit includes at least one projection dimensioned to be received in a channel of the actuator, wherein the channel of the actuator includes a plurality of detent positions, and wherein the at least one projection of the second conduit is configured to move between the plurality of detent positions as the actuator pivots about the second axis.

2. The suction handle of claim 1, wherein the first bore and the second bore are centered with respect to the first axis.

3. The suction handle of claim 1, wherein the first conduit is adapted to be coupled to an oral care device.

4. The suction handle of claim 1, wherein the first conduit and the second conduit together define a valve.

5. The suction handle of claim 1, wherein the first conduit includes at least one transverse opening in fluid communication with the first bore.

6. The suction handle of claim 1, wherein the actuator includes a third actuator position between the first actuator position and the second actuator position in which the first bore is at least partially in fluid communication with the second bore.

7. The suction handle of claim 1, wherein the second conduit includes a first section having a first cross-sectional area and a second section having a second cross-sectional area that is less than the first cross-sectional area, also wherein the first conduit includes a first section dimensioned to be received in the first section of the second conduit and a second section of the first conduit dimensioned to be received in the second section of the second conduit and wherein the second section of the first conduit includes a plug.

8. The suction handle of claim 7, wherein:
   the second section of the first conduit is fully seated in the second section of the second conduit when the first conduit and the second conduit are in the first position with respect to one another, such that the first bore is not in fluid communication with the second bore, and
   the second section of the first conduit is not fully seated in the second section of the second conduit when the first conduit and the second conduit are in the second position with respect to one another, such that the first bore is in fluid communication with the second bore.

9. The suction handle of claim 1, wherein the actuator is fluidly isolated from the fluid path when the first conduit and the second conduit are in the first position and the second position.

10. The suction handle of claim 1, wherein the first conduit is coupled to the housing and the second conduit is movable with respect to the first conduit and the housing.

11. The suction handle of claim 1, wherein the actuator is coupled to the housing and pivots with respect to the housing.

12. The suction handle of claim 1, wherein the second conduit includes at least one transverse projection dimensioned to be received in a channel of the housing, and wherein the at least one transverse projection is positioned adjacent a junction between a first section and a second section of the second conduit.

13. The suction handle of claim 1, wherein the actuator includes at least one projection dimensioned to be slidably received in a channel of the housing.

14. The suction handle of claim 1, wherein the first axis lies in a plane, and wherein the actuator pivots in the plane toward or away from the first axis.

15. An oral care system comprising:
   the suction handle of claim 1;
   an oral care device coupled to a distal end of the suction handle; and
   a coupling device coupled between the suction handle and the oral device, a first portion of the coupling device adapted to be coupled to the suction handle and a second portion of the coupling device adapted to be coupled to the oral care device.

16. The suction handle of claim 1, wherein the first axis and the second axis do not intersect.

17. The suction handle of claim 1, wherein the actuator includes a rocker switch.

18. A suction handle for oral care systems, the suction handle comprising:
   a housing comprising an interior;
   a first axis oriented along a longitudinal direction;
   a first conduit positioned in the interior of the housing, the first conduit having a first bore oriented along the longitudinal direction;
   a second conduit positioned in the interior of the housing, the second conduit adapted to be coupled to the first conduit, the second conduit having a second bore oriented along the longitudinal direction, the first conduit and the second conduit being movable with respect to one another in the longitudinal direction between a first position in which the first bore and the second bore are not in fluid communication and a second position in which the first bore and the second bore are in fluid communication, the first bore and the second bore at least partially defining a fluid path; and an actuator coupled to the housing and at least one of the first conduit and the second conduit, the actuator being pivotally movable about a second axis oriented substantially perpendicularly with respect to the first axis between a first actuator position that corresponds with the first position and a second actuator position that corresponds with the second position, wherein the actuator includes at least one projection dimensioned to be slidably received in a channel of the housing, and wherein the at least one projection at least partially defines the second axis, such that the actuator is pivotally movable about the at least one projection, relative to the housing.

* * * * *